(12) United States Patent
Kim et al.

(10) Patent No.: US 10,582,947 B2
(45) Date of Patent: Mar. 10, 2020

(54) FOLLICLE TRANSFER AND TRANSPLANTATION METHOD BASED ON FOLLICULAR UNIT EXTRACTION

(71) Applicant: Electronics and Telecommunications Research Institute, Daejeon (KR)

(72) Inventors: Kyu Hyung Kim, Daegu (KR); Tae Wuk Bae, Daegu (KR); Jung Wook Suh, Daegu (KR); Soo In Lee, Daegu (KR); Eun Chang Choi, Daegu (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 321 days.

(21) Appl. No.: 15/646,317

(22) Filed: Jul. 11, 2017

(65) Prior Publication Data

US 2018/0161056 A1 Jun. 14, 2018

(30) Foreign Application Priority Data

Dec. 9, 2016 (KR) ........................ 10-2016-0167834

(51) Int. Cl.
*A61B 17/3205* (2006.01)
*A61B 17/00* (2006.01)
*A61B 17/32* (2006.01)

(52) U.S. Cl.
CPC .................. *A61B 17/32053* (2013.01); *A61B 2017/00022* (2013.01); *A61B 2017/00473* (2013.01); *A61B 2017/00477* (2013.01); *A61B 2017/00544* (2013.01); *A61B 2017/00752* (2013.01); *A61B 2017/00969* (2013.01); *A61B 2017/320064* (2013.01)

(58) Field of Classification Search
CPC .... A61B 17/32053; A61B 2017/00752; A61B 2017/00473; A61B 2017/00544; A61B 2017/320064; A61B 2017/00022; A61B 2017/00969; A61B 2017/00477
See application file for complete search history.

(56) References Cited

U.S. PATENT DOCUMENTS

| 6,461,369 B1 | 10/2002 | Kim | |
| 2002/0103500 A1* | 8/2002 | Gildenberg | A61B 17/32053 606/187 |
| 2004/0193203 A1* | 9/2004 | Pak | A61B 17/3468 606/187 |

(Continued)

FOREIGN PATENT DOCUMENTS

| KR | 10-2001-0072422 | 7/2001 |
| KR | 10-2016-0006645 | 1/2016 |

(Continued)

*Primary Examiner* — Anh T Dang
(74) *Attorney, Agent, or Firm* — Kile Park Reed & Houtteman PLLC

(57) ABSTRACT

The present invention provides a follicle transfer and transplantation method based on FUE, which provides a follicle extraction punch for transferring and transplanting a follicular unit of a scalp and loads a follicular unit, extracted by the follicle extraction punch, to the follicle extraction punch itself or transfers the extracted follicular unit to a separate needle, thereby enabling a hair transplantation operation to be relatively quickly and accurately performed.

16 Claims, 26 Drawing Sheets

(56) References Cited

U.S. PATENT DOCUMENTS

| | | | |
|---|---|---|---|
| 2006/0161179 A1* | 7/2006 | Kachenmeister | ............................ A61B 17/32053 606/133 |
| 2006/0178677 A1* | 8/2006 | Brinson | ............ A61B 17/32053 606/133 |
| 2007/0149985 A1* | 6/2007 | Cole | ................. A61B 17/32053 606/131 |
| 2016/0015424 A1* | 1/2016 | Kim | .................... A61B 17/3468 606/187 |
| 2016/0045223 A1 | 2/2016 | Kim et al. | |
| 2017/0135713 A1* | 5/2017 | Suh | .................... A61B 17/3468 |

FOREIGN PATENT DOCUMENTS

| | | |
|---|---|---|
| KR | 10-2016-0010203 | 1/2016 |
| KR | 10-2016-0020796 | 2/2016 |

* cited by examiner

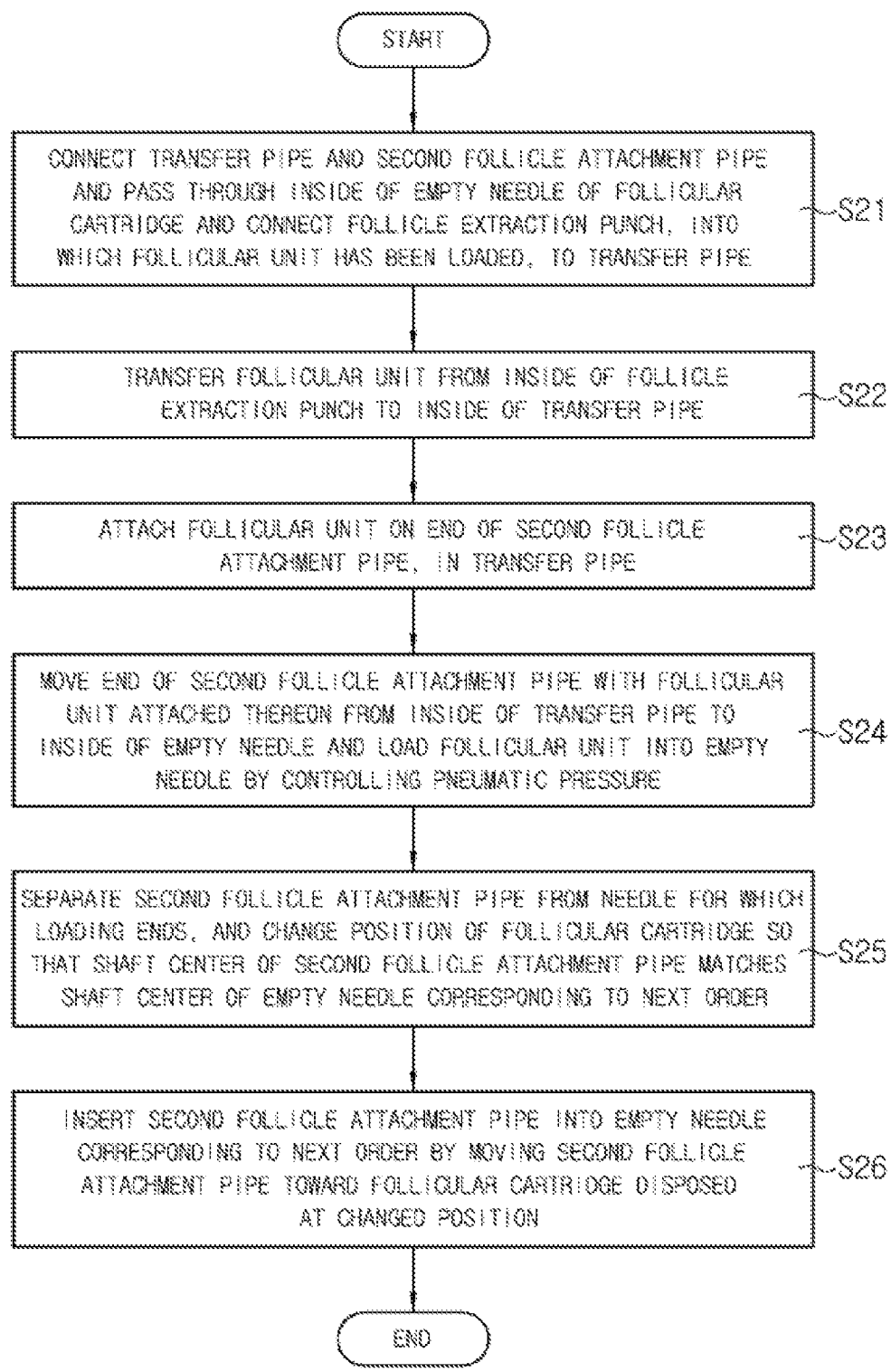

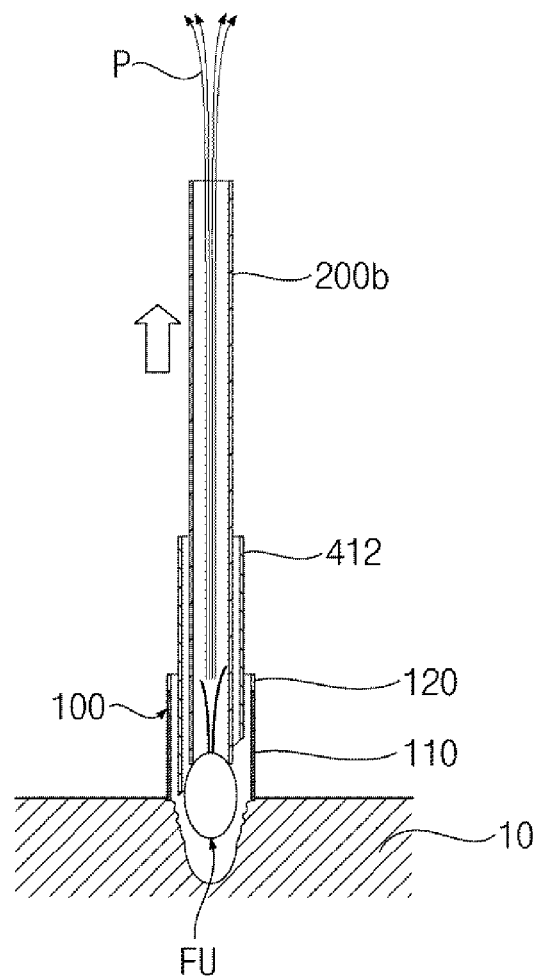

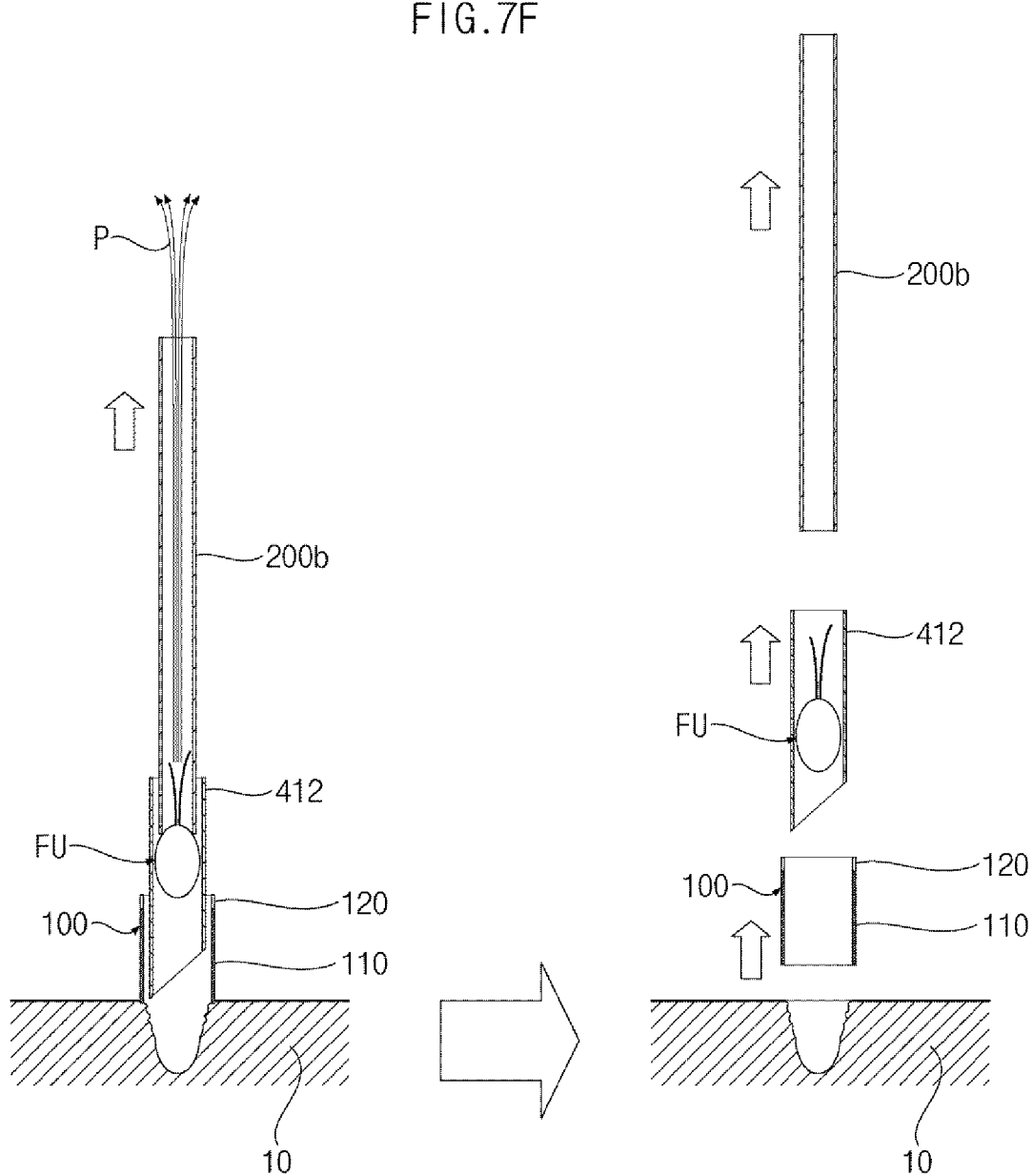

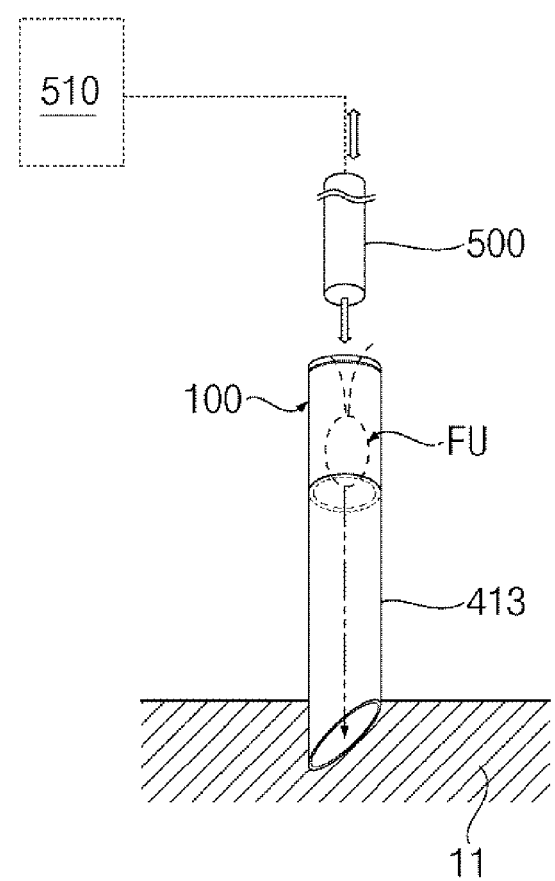

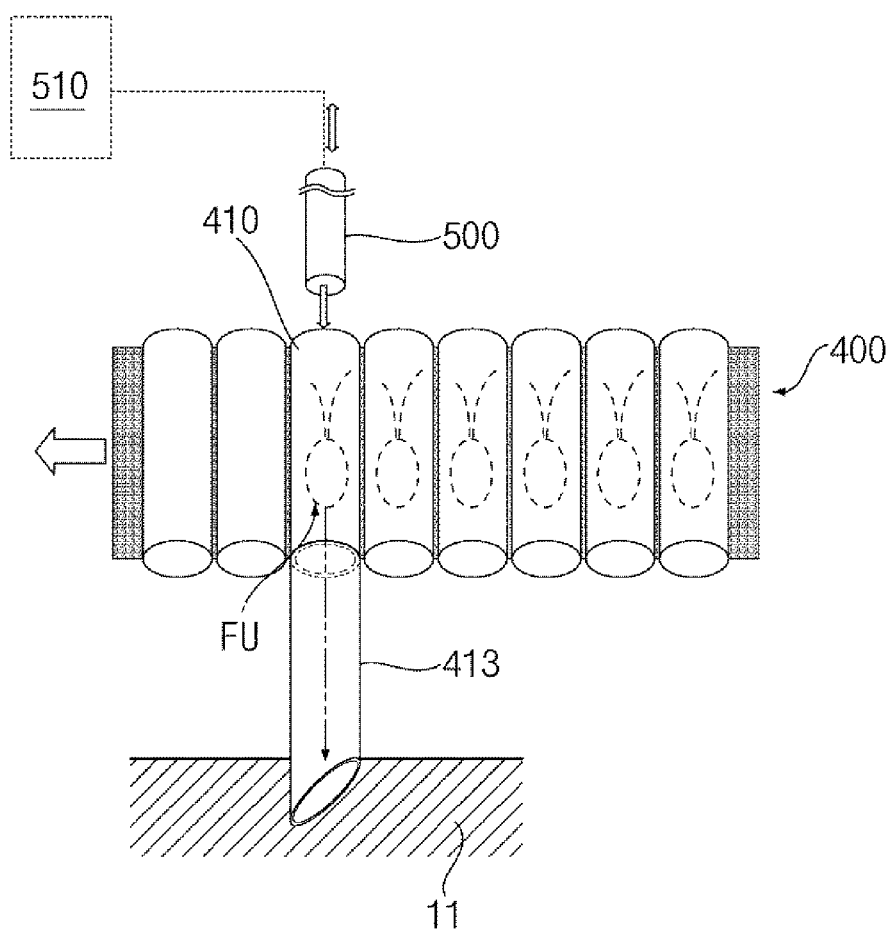

FOLLICLE TRANSFER AND TRANSPLANTATION METHOD BASED ON FOLLICULAR UNIT EXTRACTION

CROSS-REFERENCE TO RELATED APPLICATIONS

This application claims priority under 35 U.S.C. § 119 to Korean Patent Application No. 10-2016-0167834, filed on Dec. 9, 2016, the disclosure of which is incorporated herein by reference in its entirety.

TECHNICAL FIELD

The present invention relates to a follicle transfer and transplantation method based on follicular unit extraction (FUE), and more particularly, to a follicle transfer and transplantation method based on FUE, which extracts a follicular unit through FUE for transplanting hair and quickly transplant the extracted follicular unit into a scalp.

BACKGROUND

Generally, a hair transplantation operation extracts a follicle (i.e., a follicular unit) from a portion of a scalp where there are a relatively number of hairs, and transplants the extracted follicular unit into a scalp requiring hair transplantation.

The hair transplantation operation uses a strip method and an FUE method.

The strip method, a type of scalp incision method, is a method of extracting a number of follicular units by performing a surgical operation on a portion of a scalp. That is, the strip method includes a stupefaction process, a strip incision process, a suturing process, a follicular unit extraction process, and a hair transplant process using hair transplant equipment.

The FUE method of the related art, a type of non-incision method, is a method of extracting an individual follicle (i.e., a follicular unit) one by one.

For example, in a case of extracting a follicular unit, the FUE method of the related art incises a portion near a follicular unit of a scalp by using a follicular unit extraction mechanism, separates the follicular unit from the scalp by using a suction means provided as one body in the follicular unit extraction mechanism, and collects the separated follicular unit in a vessel for separately keeping the follicular unit or locates the separated follicular unit on a medical gauze.

Subsequently, the kept follicular unit may be manually transplanted by an operator or may be transplanted through an automation means.

For example, in the related art, a slit is provided near the scalp, which is a follicle transplantation target, by using a slit needle, and the follicular units collected in the vessel are arranged or are aligned on the gauze. Subsequently, the follicular units are grabbed one by one by a pincetter, and the one grabbed follicular unit is inserted into the scalp having the slit.

Particularly, in the hair transplantation operation field, the slit may denote a narrow hole which before the follicular unit is inserted into the transplantation part, is previously formed in a transplantation part of a scalp by using the slit needle or a dedicated mechanism such as a chisel having a width of 0.8 mm to 1.2 mm, or may denote a surgical operation itself of previously forming the narrow hole.

However, the FUE method of the related art causes inconvenience where after follicular units are extracted, the follicular units should be aligned near a follicular needle for transplanting the follicular units, and moreover, has a drawback where a slit needle difficult to automatically supply should be used for hair transplantation.

Moreover, in the FUE method of the related art, in a case of performing a transplantation operation by using a pincette and/or the like, since follicular units are aligned and grabbed and then are transferred by a hair transplantation needle, an action of an operator is performed twice or more for at least one follicular unit, and for this reason, much time is taken in a surgical operation, and a high-intensity skill level of the operator is needed.

Moreover, a doctor which is an operator needs a nurse or an assistant for a hair transplantation operation, and due to a long surgical operation time, a patient for which a surgical operation is to be performed has a large burden.

In the related art, the following patent document 1 discloses a follicle loading apparatus and method and discloses technology for transferring a follicular unit, previously extracted from a scalp, into a follicle supply unit.

However, the patent document 1 of the related art does not disclose a method which quickly transfers a follicular unit to the follicle supply unit in order for the follicular unit to be extracted from a scalp and directly used for hair transplantation, and for this reason, the details of the patent document 1 cannot solve a problem where a total hair transplantation operation time increases relatively.

Moreover, a patent document 2 of the related art provides only a hair transplant equipment for hair transplantation using a follicle supply pipe having the same method and structure as those of the follicle supply unit of the patent document 1, but does not disclose a method or a means for previously and effectively loading a follicular unit into the follicle supply pipe. For this reason, it is very difficult to quickly transplant a follicular unit.

PRIOR ART REFERENCE

Patent Document (patent document 1) Korean Patent Publication No. 10-2016-0010203
(patent document 1) Korean Patent Publication No. 10-2016-0020796

SUMMARY

Accordingly, the present invention provides a follicle transfer and transplantation method based on FUE, which provides a follicle extraction punch for transferring and transplanting a follicular unit of a scalp and loads a follicular unit, extracted by the follicle extraction punch, to the follicle extraction punch itself or transfers the extracted follicular unit to a separate needle, thereby enabling a hair transplantation operation to be relatively quickly and accurately performed.

In one general aspect, a follicle transfer and transplantation method based on follicular unit extraction (FUE) for extracting a follicular unit to individually locate the follicular unit in a needle includes: rotating a tip part of a follicle extraction punch contacting a scalp with respect to the follicular unit; inserting a first follicle attachment pipe into the follicle extraction punch; stopping the rotation of the tip part and attaching the follicular unit on an end of the first follicle attachment pipe with a pneumatic pressure, in the tip part; moving the first follicle attachment pipe with the follicular unit attached thereon and the follicle extraction punch to separate the follicular unit from the scalp; loading the follicular unit into the tip part of the follicle extraction punch according to control of the pneumatic pressure performed on the first follicle attachment pipe; and separating the first follicle attachment pipe from the follicle extraction punch with the follicular unit loaded thereinto.

The follicle extraction punch may include: a tip part supplied with a rotational force from a punch driver for extracting the follicular unit from the scalp; and a pipe member connecting connector provided in an end of the tip part.

The follicle transfer and transplantation method may further include, before the rotating of the tip part, movably locating the first follicle attachment pipe on the follicle extraction punch in a state where a shaft center direction of the first follicle attachment pipe matches a shaft center direction of the follicle extraction punch.

An internal diameter of the tip part of the follicle extraction punch may be set relatively greater than an external diameter of the first follicle attachment pipe so that interference of the first follicle attachment pipe is not applied to the rotation of the tip part performed with respect to the shaft center direction of the first follicle attachment pipe.

The first follicle attachment pipe may be coupled to a first pneumatic equipment which generates a pneumatic pressure in the first follicle attachment pipe.

The follicle transfer and transplantation method may further include, after the loading of the follicular unit, locating the follicle extraction punch including the follicular unit between a needle for hair transplantation and a push rod moving the follicular unit in a hair transplant equipment, forward moving the push rod toward the inside of the follicle extraction punch, moving the follicular unit of the follicle extraction punch according to the follicular unit being pushed by the push rod, and transplanting the follicular unit into the scalp via the inside of the needle for hair transplantation.

In another general aspect, a follicle transfer and transplantation method based on follicular unit extraction (FUE) for extracting a follicular unit to individually locate the follicular unit in a needle includes: connecting a transfer pipe and a second follicle attachment pipe and passing through the inside of an empty needle of a follicular cartridge and connecting the follicle extraction punch, into which the follicular unit has been loaded, to the transfer pipe; transferring the follicular unit from the inside of the follicle extraction punch to the inside of the transfer pipe; attaching the follicular unit on an end of the second follicle attachment pipe, in the transfer pipe; moving an end of the second follicle attachment pipe with the follicular unit attached thereon from the inside of the transfer pipe to the inside of an empty needle and loading the follicular unit into the empty needle by controlling a pneumatic pressure; separating the second follicle attachment pipe from the needle for which loading ends, and changing a position of the follicular cartridge so that a shaft center of the second follicle attachment pipe matches a shaft center of an empty needle corresponding to a next order; and inserting the second follicle attachment pipe into the empty needle corresponding to the next order by moving the second follicle attachment pipe toward the follicular cartridge disposed at the changed position.

The second follicle attachment pipe may be coupled to a second pneumatic equipment which generates a pneumatic pressure in the second follicle attachment pipe.

The follicle extraction punch may include: a tip part separated from a punch driver which is a rotational force generation means for extracting the follicular unit from the scalp, the tip part including an internal space into which the follicular unit is loaded; and a pipe member connecting connector provided in an end of the tip part, for connecting the follicle extraction punch to the transfer pipe.

The transfer pipe may include: a connector coupling part provided in one end of the transfer pipe, for attaching or detaching the connector of the follicle extraction punch; a pipe body part extending in a direction from the connector coupling part to the follicular cartridge and acting as a transfer path for the follicular unit; and a transfer pipe coupling part provided in another end of the transfer pipe and connected to the pipe body part to pass through the pipe body part, so that the transfer pipe coupling part becomes an entrance which an end of the second follicle attachment pipe is inserted through or detached from.

The follicular cartridge may be detachably attached on a cartridge driver which changes a position of the follicular cartridge along a direction vertical to a moving direction of the second follicle attachment pipe, with respect to a position between the transfer pipe and the second follicle attachment pipe.

The follicle transfer and transplantation method may further include, after the changing of the position of the follicular cartridge, separating the follicular cartridge, including a plurality of needles into which follicular units are respectively loaded, from the cartridge driver, mounting the separated follicular cartridge on a hair transplant equipment, locating the follicular cartridge between a needle for hair transplantation and a push rod moving the follicular unit in the hair transplant equipment, forward moving the push rod toward the inside of the needle of the follicular cartridge, moving the follicular unit of the needle of the follicular cartridge according to the follicular unit being pushed by the push rod, and transplanting the follicular unit into the scalp via the inside of the needle for hair transplantation.

In another general aspect, a follicle transfer and transplantation method based on follicular unit extraction (FUE) for extracting a follicular unit to individually locate the follicular unit in a needle includes: sequentially setting up a follicle extraction punch, a needle, and a third follicle attachment pipe with respect to an upper portion of the follicular unit; rotating a tip part of the follicle extraction punch contacting a scalp in a state where the third follicle attachment pipe and the needle are disposed in the follicle extraction punch; stopping the rotation of the tip part and attaching the follicular unit on an end of the third follicle attachment pipe with a pneumatic pressure, in the tip part; moving the third follicle attachment pipe with the follicular unit attached thereon to separate the follicular unit from the scalp; and loading the follicular unit into the needle through control of the pneumatic pressure and separating the third follicle attachment pipe and the follicle extraction punch from the needle.

An internal diameter of the tip part of the follicle extraction punch may be set relatively greater than an external diameter of the needle so that interference of the needle is not applied to the rotation of the tip part performed with respect to a shaft center direction of the needle, and an internal diameter of the needle may be set relatively greater than an external diameter of the third follicle attachment pipe so that the third follicle attachment pipe is inserted into the needle.

The needle may have a structure where a circular border is provided in one end of the needle and a wedge type border is provided another end, so as to be used as a needle for hair transplantation.

The needle may have a structure where a circular border is provided in each of one end and another end of the needle, so as to be used as a needle for hair transplantation.

Other features and aspects will be apparent from the following detailed description, the drawings, and the claims.

BRIEF DESCRIPTION OF THE DRAWINGS

FIG. 1 is a flowchart for describing a method of loading a follicular unit to a follicle extraction punch in a follicle transfer and transplantation method based on FUE according to an embodiment of the present invention.

FIGS. 7A to 7F are conceptual diagrams of respective operations of the method illustrated in FIG. 6.

FIG. 8 is a conceptual diagram for describing a method of transplanting a follicular unit, loaded by the method of FIG. 1, of a follicle extraction punch to a scalp.

FIG. 9 is a conceptual diagram for describing a method of transplanting a follicular unit, loaded by the method of FIG. 3, from a follicle extraction punch to a scalp.

DETAILED DESCRIPTION OF EMBODIMENTS

Figure 2A:
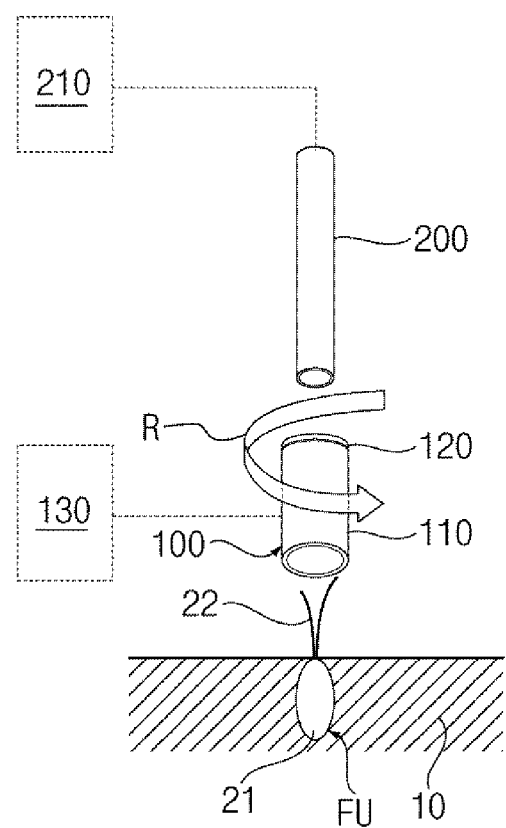
FIGS. 2A to 2F are conceptual diagrams of respective operations of the method illustrated in FIG. 1.

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

The terms used herein are for the purpose of describing particular embodiments only and are not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Hereinafter, embodiments of the present invention will be described in detail with reference to the accompanying drawings.

FIG. 1 is a flowchart for describing a method of loading a follicular unit to a follicle extraction punch in a follicle transfer and transplantation method based on FUE according to an embodiment of the present invention. FIGS. 2A to 2F are conceptual diagrams of respective operations of the method illustrated in FIG. 1.

Referring to FIG. 1, the present embodiment discloses the follicle transfer and transplantation method based on FUE in which a follicular unit is extracted and individually located in a needle. In detail, the present embodiment may provide a hair transplantation method, including a follicular unit extraction method, a follicular unit transfer method, and a follicular unit transplantation method, and a means relevant thereto.

The present embodiment relates to a method of extracting follicular units, and in more detail, provides a series of processes of extracting a follicular unit and loading the follicular unit into a follicle extraction punch.

For example, the present embodiment may include an operation (S11) of rotating a tip part of a follicle extraction punch contacting a scalp with respect to a follicular unit and an operation (S12) of inserting a first follicle attachment pipe into the follicle extraction punch.

Subsequently, an operation (S13) of stopping the rotation of the tip part and attaching a follicular unit on an end of the first follicle attachment pipe with a pneumatic pressure in the tip part may be performed.

When the follicular unit has been attached on the first follicle attachment pipe, an operation (S14) of moving the follicle extraction punch and the first follicle attachment pipe with the follicular unit attached thereon to separate the follicular unit from the scalp, an operation (S15) of loading the follicular unit into the tip part of the follicle extraction punch by controlling the pneumatic pressure for the first follicle attachment pipe, and an operation (S16) of separating the first follicle attachment pipe from the follicle extraction punch with the follicular unit loaded thereinto may be performed.

As a result, since a follicular unit is individually extracted, the follicular unit may be immediately stored or located in the follicle extraction punch without being transferred to the inside of another storage vessel and may be used for hair transplantation, thereby considerably simplifying a process of extracting, transferring, and transplanting the follicular unit and shortening a time taken in the extracting, transferring, and transplanting process. That is, as described below with reference to FIG. 8, the follicle extraction punch with the follicular unit loaded thereinto may be directly used for hair transplantation along with a needle, having a shaft center direction matching that of the follicle extraction punch, for hair transplantation.

A detailed means for realizing the operations will be disclosed with reference to FIGS. 2A to 2F.

Referring to FIGS. 1 and 2A, for the operation (S11) of rotating the tip part of the follicle extraction punch, the present embodiment may include a follicle extraction punch 100, a punch driver 130, a first follicle attachment pipe 200, and a first pneumatic equipment 210.

The follicular unit FU may include a hair bulb member 21 having a diameter greater than an internal diameter of the first follicle attachment pipe 200 and a hair member 22 extending from a rear end of the hair bulb member 21, within a size range capable of being inserted into the follicle extraction punch 100.

The follicle extraction punch 100 and the first follicle attachment pipe 200 may each have a follow type.

For example, the follicle extraction punch 100 may include a tip part 110, which is supplied with a rotational force from the punch driver 130 for extracting the follicular unit FU from a scalp 10, and a pipe member connecting connector 120 provided in an end of the tip part 110.

An internal diameter of the tip part 110 of the follicle extraction punch 100 may be set relatively greater than an external diameter of the first follicle attachment pipe 200 in order for interference of the first follicle attachment pipe 200 not to be applied to a rotation of the tip part 110 performed with respect to a shaft center direction of the first follicle attachment pipe 200.

The punch driver 110 may be a device or a medical operation equipment corresponding thereto, which generates a rotational force necessary for extracting the follicular unit FU from the scalp 10.

The punch driver 130 may use an electrical motor or a pneumatic motor as a driving source and may be a means which generates the rotational force by using the driving source according to a control signal of a controller (not shown).

The punch driver 130, although not shown, may further include a supporting means for raising or lowering the follicle extraction punch 100 while guiding a rotation of the follicle extraction punch 100 and a rotation force transfer means for transferring the rotational force of the driving source to the follicle extraction punch 100.

The supporting means of the punch driver 130 may include a linear guide and movement device, a mounting part which is provided in an end of the movement device and is coupled to the follicle extraction punch 100 in a plug and socket attachment/detachment type, and a bearing device which is provided in the mounting part. However, this is merely an exemplary configuration, and the supporting means may be implemented as various types.

The rotational force transfer means of the punch driver 130 may include one or more driving rotation mechanical elements such as a gear, a pulley, a belt, a chain, a friction wheel, etc. for transferrin the rotational force like a drill device. Although shown in the tip part 110 of the follicle extraction punch 100, a driven rotation mechanical element and a brake device (not shown) coupled to each other for receiving the rotational force in correspondence with the punch driver 130 may be provided.

Therefore, the tip part 110 of the follicle extraction punch 100 may rotate R with the rotational force transferred from the punch driver 130, or when the rotational force is not transferred from the punch driver 130, the tip part 110 may be stopped by the brake device.

A lower portion of the tip part 110 may be configured with a drill bit which incises the scalp 10 near the follicular unit FU along a circumference direction of the follicle unit FU, or may be configured with a punching means which hits the scalp 10 near the follicular unit FU along a lengthwise direction of the follicular unit FU so as to separate the follicular unit FU from the scalp 10.

An upper portion of the tip part 110 may be configured with a hollow shaft member connecting adaptor or the connector 120 such as a coupler.

The inside of the first follicle attachment pipe 200 may be hollow along the shaft center direction, and thus, a movement of air or an action of a pneumatic pressure P (for example, a sucking force or a sound pressure) may be performed in the first follicle attachment pipe 200.

To this end, the first follicle attachment pipe 200 may be coupled to the first pneumatic equipment 210 through a pneumatic hose so as to receive the pneumatic pressure P from the first pneumatic equipment 210. Here, although devices using the pneumatic pressure described in the present embodiment in addition to the first pneumatic equipment 210 are not shown, the first follicle attachment pipe 200 may include general pressure control means such as a pump, a filter, an electronic valve, a regulator, a pneumatic controller, etc.

The first follicle attachment pipe 200 may move in a lengthwise direction of the follicle extraction punch 100 with respect to a shaft center of the follicle extraction punch 100 and may be provided longer than the follicle extraction punch 100.

The control of the pneumatic pressure by the first pneumatic equipment 210 on the first follicle attachment pipe 200 may denote a series of control processes where the follicle unit FU is temporarily attached on an end of the first follicle attachment pipe 200 with the pneumatic pressure P such as a sucking force, and then, when the end of the first follicle attachment pipe 200 and the follicular unit FU move to the inside of the follicle extraction punch 100, by minimizing the pneumatic pressure P (for example, by removing the sucking force), the follicular unit FU may be loaded to the inside of the tip part 110 (i.e., the inside of the follicle extraction punch 100). Here, the loading may denote that the follicular unit FU is stably disposed in the follicle extraction punch 100 or the tip part 110 by a frictional force applied to a contact surface such as an inner circumference surface of the follicle extraction punch 100, and if there is no excessive shaking or external force relatively greater than the frictional force, the follicular unit FU is stably located in the tip part 110.

The first pneumatic equipment 210 may be configured with a device means that generates the pneumatic pressure P in the first follicle attachment pipe 200 or controls a level of the pneumatic pressure P.

Furthermore, as illustrated in FIG. 2A, in a state where the shaft center direction of the first follicle attachment pipe 200 matches the shaft center direction of the follicle extraction punch 100, an operation where the first follicle attachment pipe 200 is movably disposed on the follicle extraction punch 100 may be performed before the operation (S11) of rotating the tip part of the follicle extraction punch.

Figure 2B:
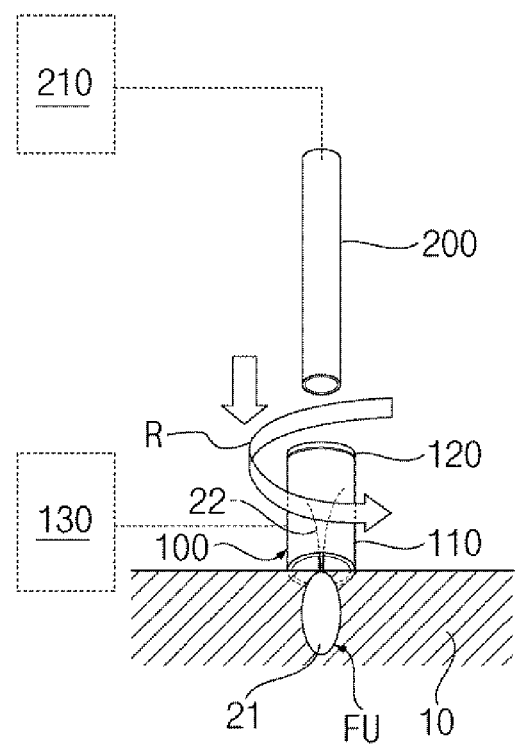

Subsequently, as illustrated in FIG. 2B, the tip part 110 of the follicle extraction punch 100 of FIG. 2A may rotate R in contact with the scalp 10. The rotation R of the tip part 110 may denote a series of medical operations for follicular unit extraction for collecting the follicular unit FU from the scalp 10.

Figure 2C:
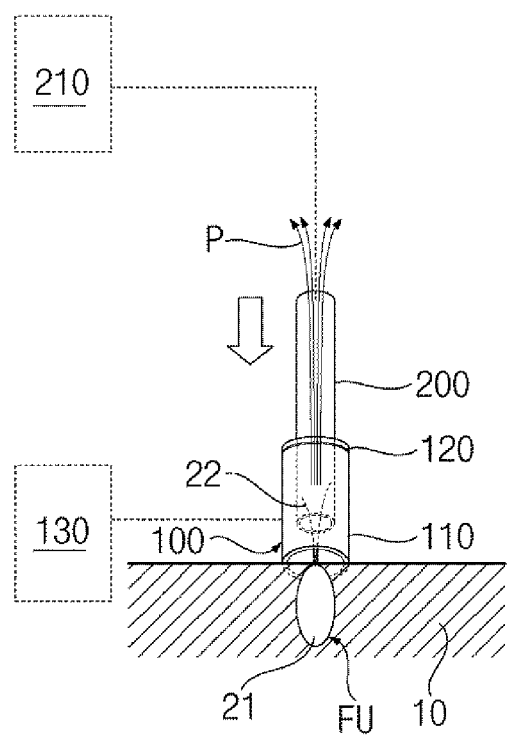

Referring to FIGS. 2B and 2C, in the operation (S12) of inserting the first follicle attachment pipe of FIG. 1, an end of the first follicle attachment pipe 200 may be inserted into the follicle extraction punch 100 while the tip part 110 of the follicle extraction punch 100 is rotating R. Subsequently, the rotation of the tip part 110 may stop.

Figure 2D:
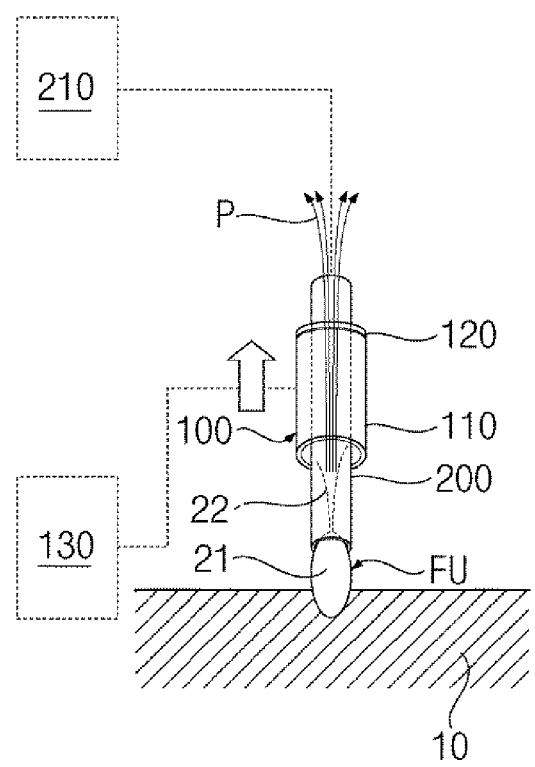

Referring to FIGS. 2C and 2D, the operation (S13) of attaching the follicular unit FU on the end of the first follicle attachment pipe 200 with the pneumatic pressure P in the tip part 110 of the follicle extraction punch 100 may be performed. That is, the first pneumatic equipment 210 may generate the pneumatic pressure P in the first follicle attachment pipe 200. In this case, the hair member 22 of the follicular unit FU may move to an internal space of the end of the first follicle attachment pipe 200, but since the hair bulb member 21 of the follicular unit FU has a diameter greater than an internal diameter of the first follicle attachment pipe 200, the hair bulb member 21 of the follicular unit FU may contact a border of the end of the first follicle attachment pipe 200, whereby the hair bulb member 21 may be maintained in a state of being attached on the end of the first follicle attachment pipe 200 according to an action of the pneumatic pressure P maintained as a predetermined pressure.

Figure 2E:
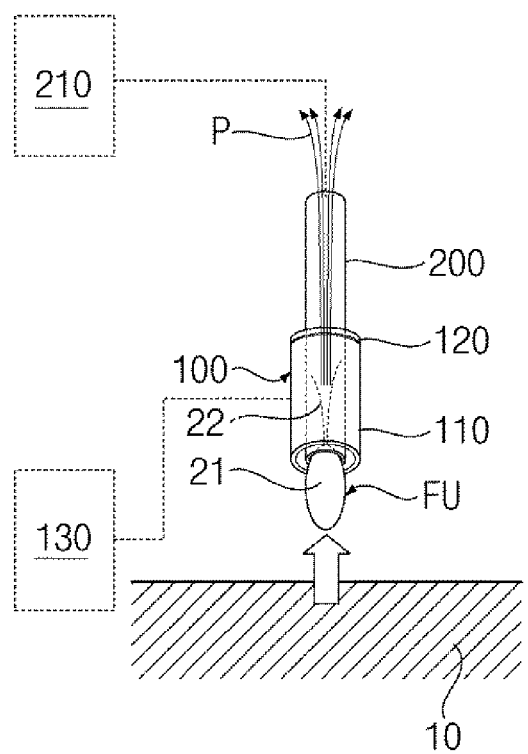

Referring to FIGS. 2D and 2E, the operation (S14) of separating the follicular unit FU from the scalp 10 may be performed. That is, the follicle extraction punch 100 and the first follicle attachment pipe 200 with the follicular unit FU attached thereon may move in a direction deviating from the scalp 10, and thus, the follicular unit FU may be separated from the scalp 10.

Subsequently, referring to FIGS. 2E and 2F, the operation (S15) of loading the follicular unit into the tip part of the follicle extraction punch and the operation (S16) of separating the first follicle attachment pipe from the follicle extraction punch with the follicular unit loaded thereinto may be performed.

Although not shown, the movement or separation of the first follicle attachment pipe 200 or the movement (for example, raising to be separated from the scalp) of the follicle extraction punch 100 may be performed by a linear transfer mechanism or a raising/lowering operation device connectable to the follicle extraction punch 100 and the first follicle attachment pipe 200, or may be performed by using an attractive force of a worker.

That is, the first follicle attachment pipe 200 with the follicular unit FU attached thereon may move (for example, raise) by a predetermined distance in the follicle extraction punch 100, and then, may stop.

Therefore, the follicular unit FU may be located in the tip part 110 of the follicle extraction punch 100. When the follicular unit FU is located in the tip part 110, the first pneumatic equipment 210 may remove or minimize the pneumatic pressure P supplied to the first follicle attachment pipe 200.

In this case, the follicular unit FU may be separated from the end of the first follicle attachment pipe 200, and the separated follicular unit FU may be disposed in the tip part 110 of the follicle extraction punch 100.

Subsequently, the first follicle attachment pipe 200 may be separated from the follicle extraction punch 100, and only the follicular unit FU may remain in the follicle extraction punch 100.

The follicle extraction punch 100 where the follicle unit FU is individually loaded or disposed may be separated from the punch driver 130, and then, may be used for a follicular unit transfer method of FIG. 3 or a follicular unit transplantation method of FIG. 8 to be described below.

Figure 2F:
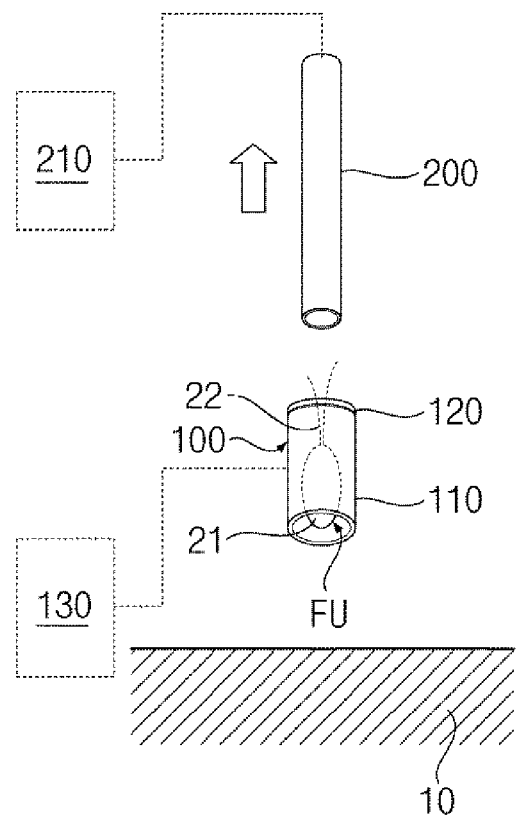
Figure 3:
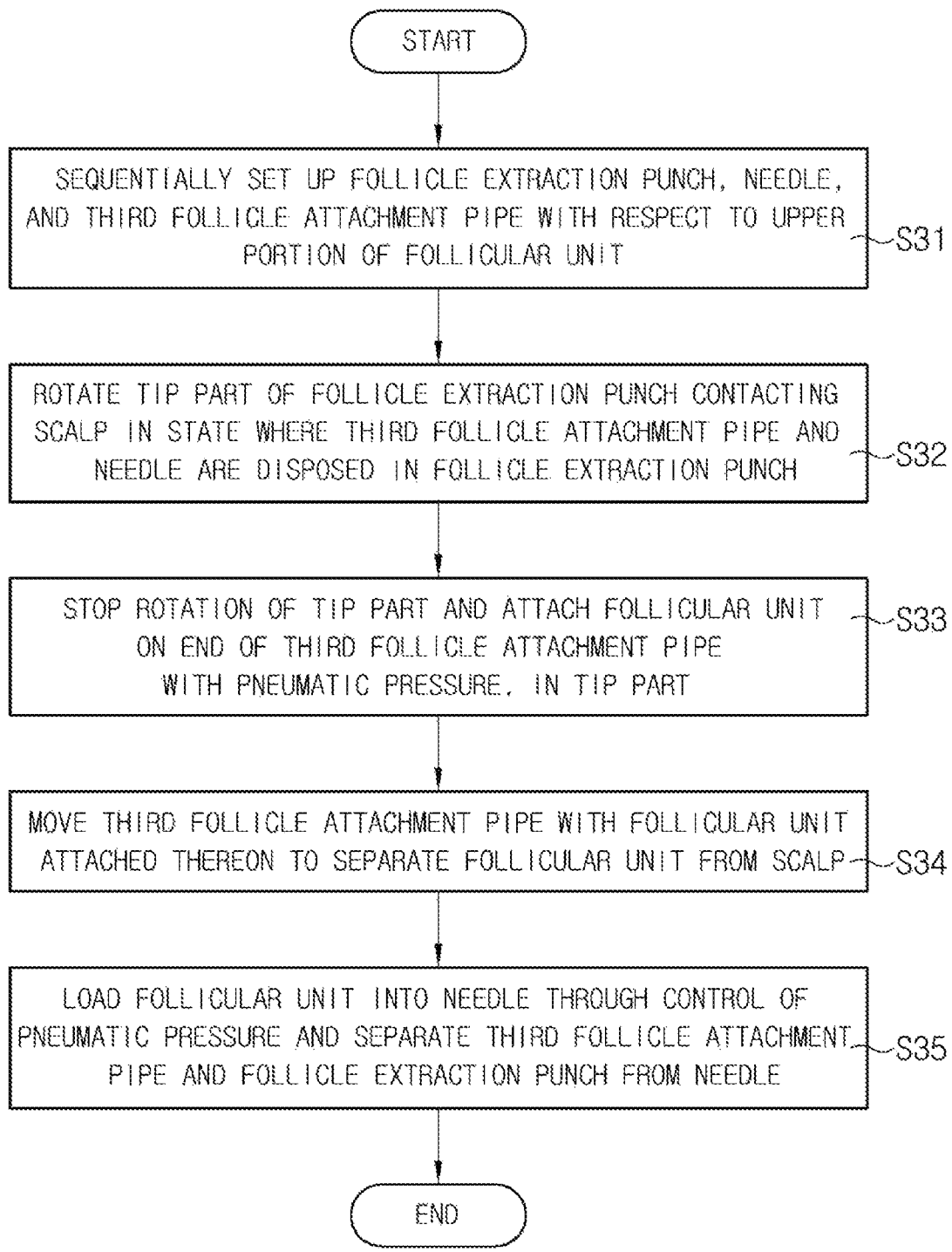
FIG. 3 is a flowchart for describing a method of loading a follicular unit from a follicle extraction punch to a needle illustrated in FIG. 2F.

FIG. 3 is a flowchart for describing a method of loading a follicular unit from a follicle extraction punch to a needle illustrated in FIG. 2F. FIGS. 4A to 4F are conceptual diagrams of respective operations of the method illustrated in FIG. 3.

FIG. 3 illustrates a method of extracting follicular units FU and individually locating the follicular units FU in a plurality of needles 410 of a follicular cartridge 400, and particularly, discloses detailed operations for quickly and safely transferring the follicular units FU of the follicle extraction punch 100 to the needles 410.

Here, the needle 410 may be provided in plurality or as a predetermined number for each cartridge unit, and the needles 410 may be arranged in the follicle cartridge 400.

For example, the needle 410 may be used as a needle for the supply of follicular units, and in this case, may have a structure (i.e., a tube type structure) where a circular border is provided in each of one end and the other end of the needle 410.

However, in terms of a needle used for hair transplantation, the needle 410 may be applied or used for the general-purpose, and thus, may perform various functions such as the supply, transfer, or transplantation of follicular units.

Figure 4A:
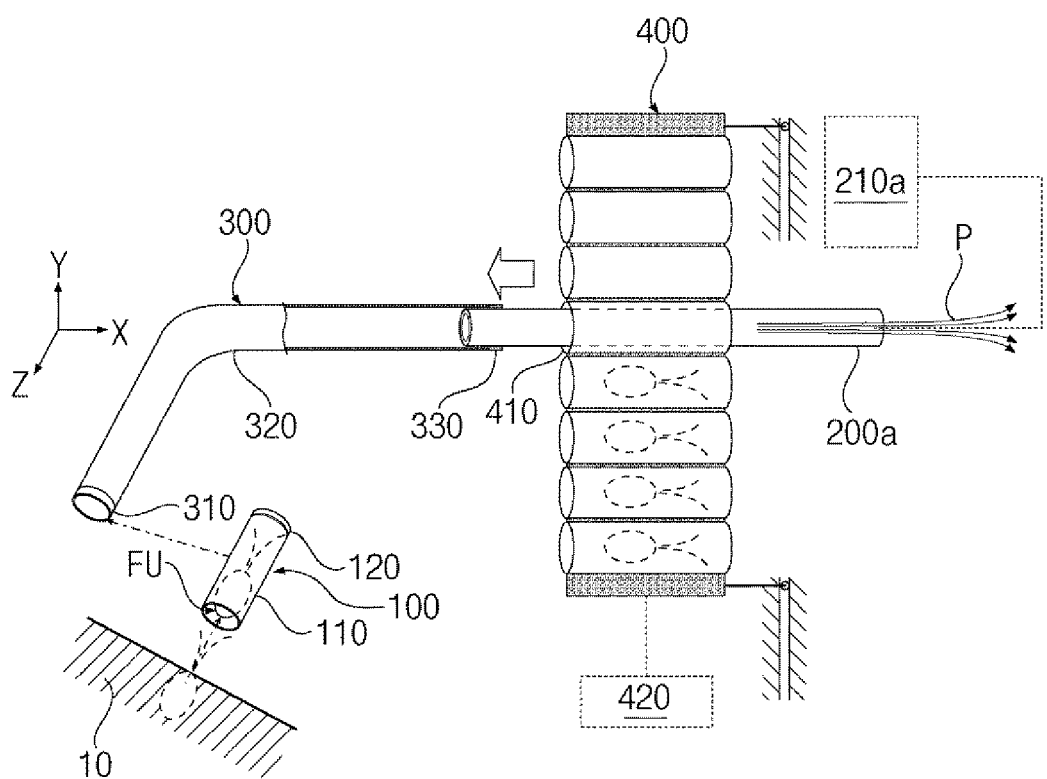
FIGS. 4A to 4F are conceptual diagrams of respective operations of the method illustrated in FIG. 3.

Referring to FIGS. 3 and 4A, the present embodiment may include an operation (S21) of connecting a second follicle attachment pipe 200a and a transfer pipe 300 passing through the inside of an empty needle 410 of a follicular cartridge 400 and connecting the follicle extraction punch 100, into which the follicular unit FU has been loaded, to the transfer pipe.

Here, the follicle extraction punch 100 with the follicle unit FU loaded thereinto may be prepared by the method described above with reference to FIGS. 1 to 2F and may move toward the transfer pipe 300. That is, the follicle extraction punch 100 may include: the tip part 110 which includes an internal space into which the follicular unit FU is loaded, and is separated from the punch driver 130 (see FIG. 2F) which is a rotational force generation means for extracting the follicular unit FU from the scalp 10; and the pipe member connecting connector 120 which is provided in an end (for example, an upper end) of the tip part 110 for connecting the follicle extraction punch 100 to the transfer pipe 300.

Moreover, the second follicle attachment pipe 200a may have a configuration which is the same as or similar to the above-described first follicle attachment pipe. Also, the second follicle attachment pipe 200a may be coupled to a second pneumatic equipment 210a which generates a pneumatic pressure P in the second follicle attachment pipe 200a or generates the pneumatic pressure P in the second follicle attachment pipe 200a and the transfer pipe 300. For example, the second pneumatic equipment 210a may a device having an operation capacity which greater than that of the first pneumatic equipment.

Particularly, the transfer pipe 300 may include a connector coupling part 310 which is provided in one end of the transfer pipe 300, for attaching or detaching the connector 120 of the follicle extraction punch 100.

Moreover, the transfer pipe 300 may include a pipe body part 320 which extends in a direction from the connector coupling part 310 to the follicular cartridge 400 and acts as a transfer path for the follicular unit FU.

Moreover, the transfer pipe 300 may include a transfer pipe coupling part 330 which is connected to the pipe body part 320 to pass through the pipe body part 320 and is provided in the other end of the transfer pipe 300, so as to act as an entrance which an end of the second follicle attachment pipe 200a is inserted through or detached from.

Here, an internal diameter of each of the pipe body part 320 and the transfer pipe coupling part 330 may be set to have a size corresponding to a sum of an external diameter of the second follicle attachment pipe 200a and an insertion tolerance or a gap size. Also, the internal diameter of the transfer pipe coupling part 300 may be set to have a size corresponding to an internal diameter of the needle 410.

The follicular cartridge 400 may be disposed with respect to a position between the transfer pipe 300 and the second follicle attachment pipe 200a.

The follicular cartridge 400 may include a cartridge side surface which is open and matches a direction in which the needle 410 is opened, and thus, when the second follicle attachment pipe 200a moves toward the follicular cartridge 400, the follicular cartridge 400 may pass through a corresponding empty needle 410 and move toward the transfer pipe 300.

Moreover, the follicular cartridge 400 may be detachably attached on a cartridge driver 420 which changes a position of the follicular cartridge 400 along a direction (for example, a Y axis direction) vertical to a moving direction (for example, a lengthwise direction or an X axis direction) of the second follicle attachment pipe 200a.

The cartridge driver 420 may sequentially move or stop a moving plate, on which the follicular cartridge 400 is detachably attached, by using a linear guide device and a driving device.

Figure 4B:
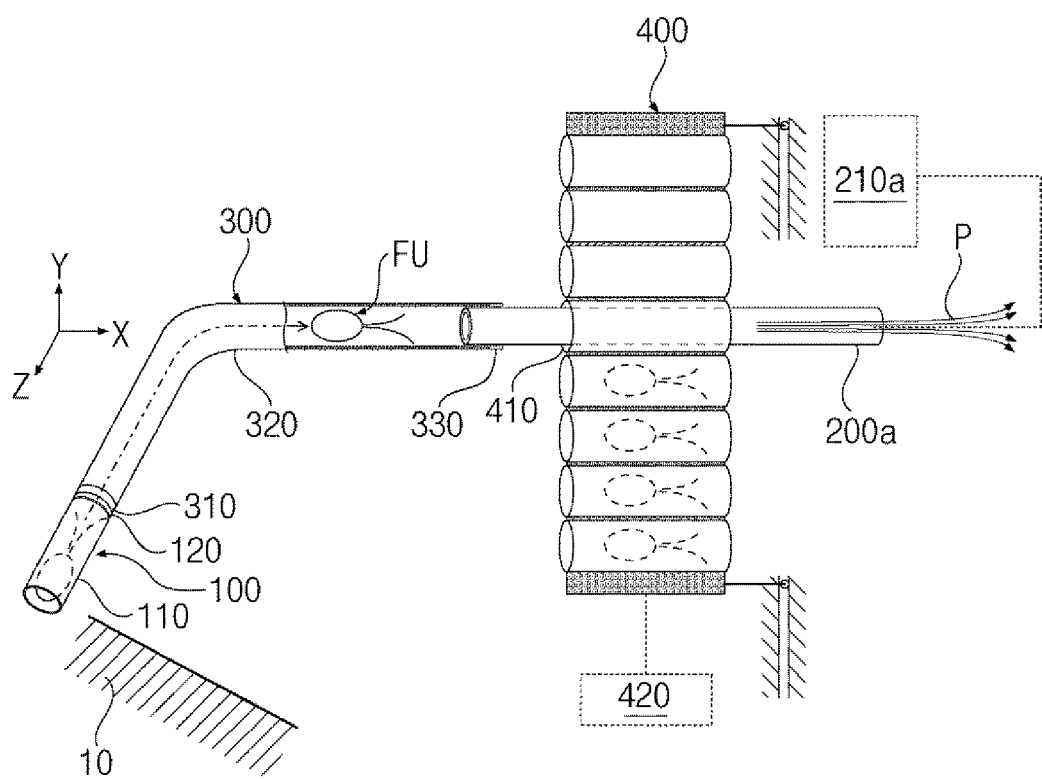

As a result, as illustrated in FIG. 4B, the follicle extraction punch 100 with the follicular unit FU loaded thereinto may be connected to the transfer pipe 300 through the connector 120 and the connector coupling part 310.

Referring to FIGS. 3 and 4B, the pneumatic pressure P may be generated in the second pneumatic equipment 210a and may be applied to the inside of the tip part 110 of the follicle extraction punch 100 which is spatially connected to the inside of the transfer pipe 300 and the second follicle attachment pipe 200a.

Therefore, an operation (S22) of transferring the follicular unit FU from the inside of the follicle extraction punch 100 to the inside of the transfer pipe 300 may be performed.

Due to a continued action of the pneumatic pressure P, the follicular unit FU may reach an end of the second follicle attachment pipe 200a.

Figure 4C:
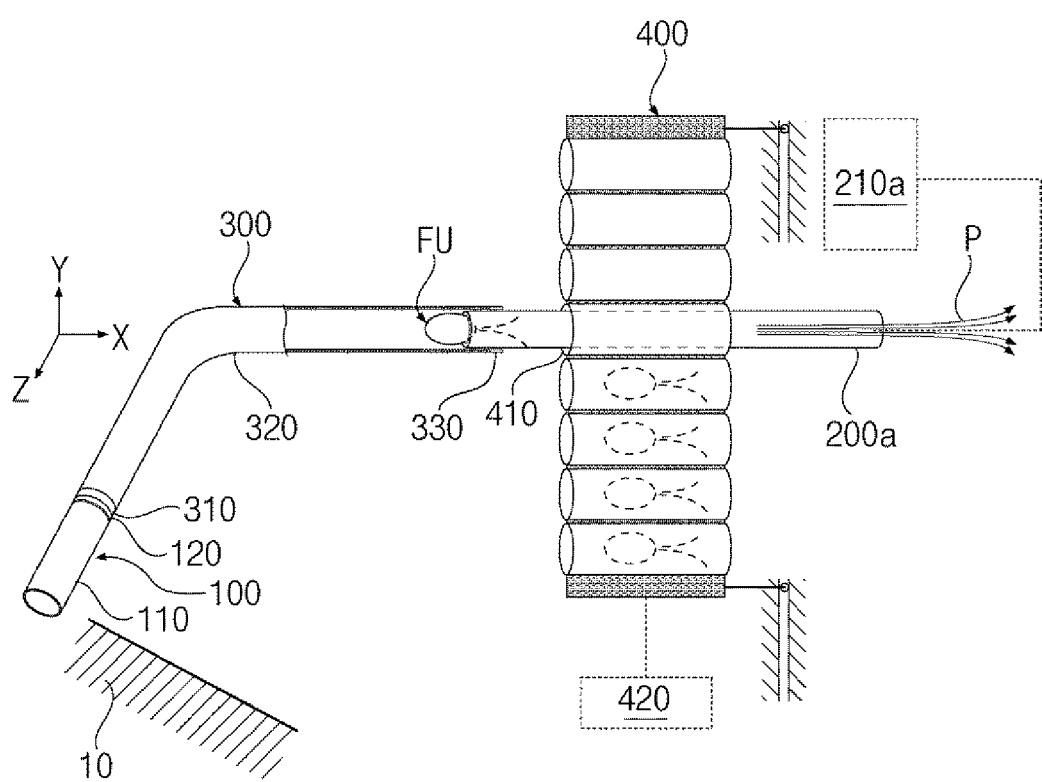

Accordingly, an operation (S23) of attaching the follicular unit FU on the end of the second follicle attachment pipe 200a in the transfer pipe 300 may be performed as in FIG. 4C.

Figure 4D:
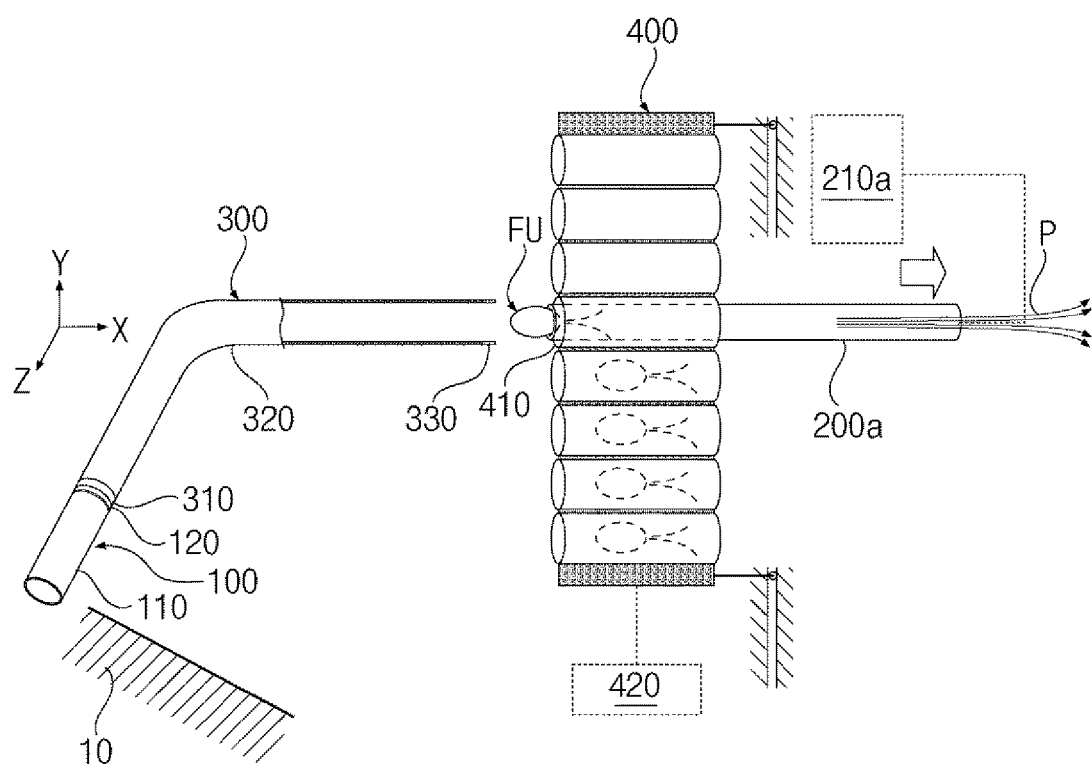
Figure 4E:
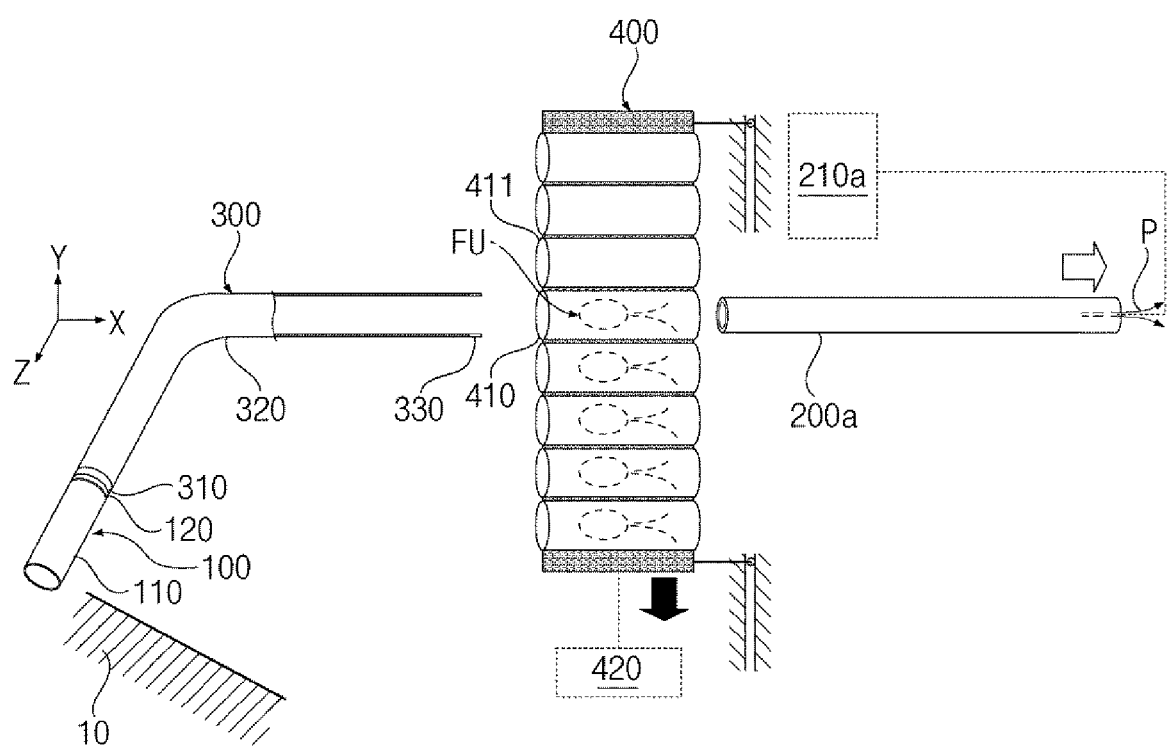

Referring to FIGS. 4D and 4E, a whole portion of the second follicle attachment pipe 200a with the follicular unit FU attached thereon may backward move from the inside of a corresponding needle 410 of the follicular cartridge 400, and thus, may be separated from the transfer pipe coupling part 330 of the transfer pipe 300.

Subsequently, an operation (S24) of moving an end of the second follicle attachment pipe 200a with the follicular unit FU attached thereon from the inside of the transfer pipe 300 to the inside of an empty needle 410 and loading the follicular unit FU into the empty needle 410 by controlling a pneumatic pressure may be performed.

That is, when the end of the second follicle attachment pipe 200a with the follicular unit FU attached thereon reaches the inside of the needle 410, the backward movement of the second follicle attachment pipe 200a may stop.

Subsequently, the second pneumatic equipment 210a may minimize (for example, removing a sucking force) the pneumatic pressure P, and thus, the follicular unit FU may be loaded into or stably disposed in a corresponding needle 410.

The second follicle attachment pipe 200a may continuously backward move again to completely move to an outer position of the needle 410 or an outer position of the follicular cartridge 400, and then, may stop.

Figure 4F:
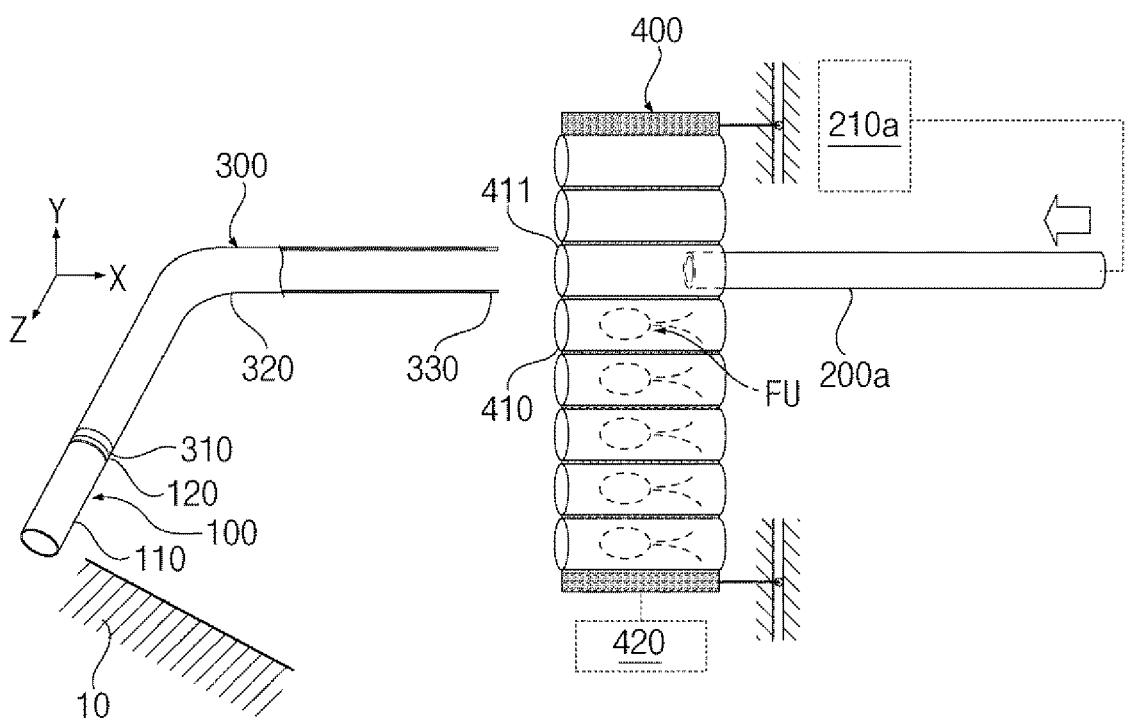

Referring to FIGS. 4E and 4F, an operation (S25) of separating the second follicle attachment pipe 200a from the needle 410 for which loading ends as described above, and then, changing a position of the follicular cartridge 400 in order for a shaft center of the second follicle attachment pipe 200a to match a shaft center of an empty needle 411 corresponding to a next order may be performed.

That is, when the second follicle attachment pipe 200a backward moves and is completely separated from an outer side of the follicular cartridge 400, the cartridge driver 420 may move the follicular cartridge 400 in the Y axis direction by a stroke distance corresponding to a needle disposition interval, and when the second follicle attachment pipe 200a reaches a position capable of being inserted into an empty needle 411 corresponding to a next order, the cartridge driver 420 may control a cartridge displacement for stopping the follicular cartridge 400.

The control of the cartridge displacement by the cartridge driver 420 may be sequentially or repeatedly performed until all empty needles 411 are filled with follicular units FU.

Referring to FIG. 4F, an operation (S26) of inserting the second follicle attachment pipe 200a into the empty needle corresponding to the next order by moving the second follicle attachment pipe 200a toward the follicular cartridge 400 disposed at the changed position may be performed.

Subsequently, the method may again return to the operation (S21) of FIG. 4A and may repeat the above-described details, and thus, the follicular units FU may be loaded into all the needles 410 and 411 of the follicular cartridge 400.

To briefly describe the details, the method of transferring the follicular unit FU may use the transfer pipe 300 and may individually keep the follicular units FU in the respective needles 410 and 411. To this end, the follicular unit FU which is separated and extracted from the scalp 10 by a rotational motion of the follicle extraction punch 100 and the pneumatic pressure P may move from the follicle extraction punch 100 to the transfer pipe 300, and the second follicle attachment pipe 200a may forward move to pass through the needle 410 of the follicular cartridge 400 and may move to the inside of the transfer pipe 300. Also, the follicular unit FU may be adhered to the end of the second follicle attachment pipe 200a by the pneumatic pressure P, in the transfer pipe 300. The follicular unit FU and the second follicle attachment pipe 200a may backward move and may be located in the needle 410 of the follicular cartridge 400. By controlling the pneumatic pressure, the follicular unit FU may be stably located in a corresponding needle 410 of the follicular cartridge 400, and then, the second follicle attachment pipe 200a may backward move continuously and may be separated from the corresponding needle 410. At this time, in order for a follicular unit FU corresponding to a next order to be stably located in a needle 411 corresponding to a next order, the needles 410 and 411 may sequentially move according to the movement of the follicular cartridge 400. Subsequently, the second follicle attachment pipe 200a may forward move toward the inside of the transfer pipe 300 via the needle 411 corresponding to the next order again.

Figure 5A:
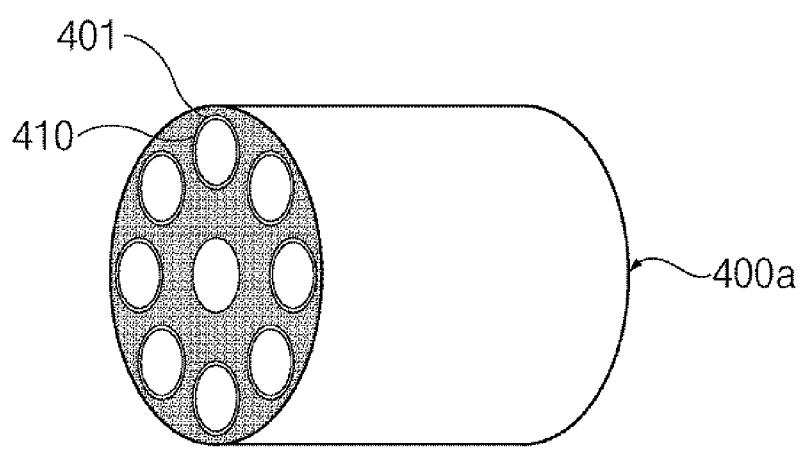
FIG. 5A is a perspective view illustrating a modification example of a follicular cartridge illustrated in FIG. 4A.
Figure 5B:
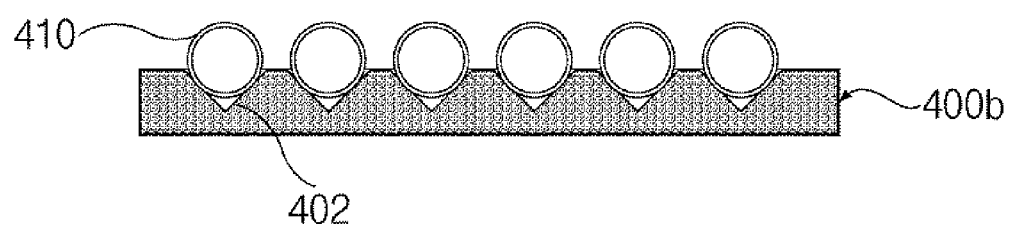
FIGS. 5B and 5C are cross-sectional views illustrating other modification examples of a follicular cartridge illustrated in FIG. 4A.
Figure 5C:
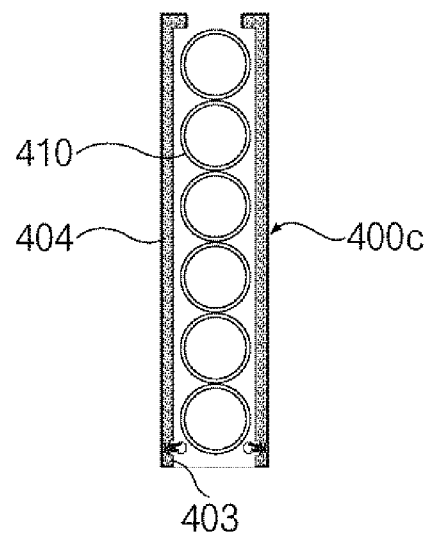

FIG. 5A is a perspective view illustrating a modification example of a follicular cartridge illustrated in FIG. 4A. FIGS. 5B and 5C are cross-sectional views illustrating other modification examples of a follicular cartridge illustrated in FIG. 4A.

Referring to FIG. 5A, a follicular cartridge 400a according to an application example may be disposed between the transfer pipe and the second follicle attachment pipe described above and may be a cylindrical type structure including a plurality of needle positioning holes 401 which are opened in the same direction, in order to arrange the plurality of needles 410 in a circumference direction. Each of the needles 410 may be loadably or unloadably inserted into one corresponding needle positioning hole 401 of the plurality of needles 410.

Particularly, in the present embodiment, in a case where a cylindrical type follicular cartridge 400a is applied, the above-described cartridge driver 420 illustrated in FIG. 4F may also be modified into and designed as a driving device that supports a rotary loading method.

The present embodiment may provide another follicular cartridge 400b corresponding to a plate type structure where a plurality of needle positioning grooves 401 are arranged at certain intervals in a lengthwise direction.

Moreover, the present embodiment may provide another follicular cartridge 400c having a magazine type. Here, the follicular cartridge 400c may include a needle unloading port 403 for loading and unloading of the needle 410 and a casing 404 where the needle unloading port 403 is provided. Both side surfaces of the casing 404 of the follicular cartridge 404 corresponding to an opened direction of the needle 410 may also be opened, and thus, the second follicle attachment pipe 200a may be loaded into or unloaded from the inside of the needle 410 of the follicular cartridge 400c. For example, although not shown, a needle temporary fixing means or a needle unloading means using an elastic force of an elastic member may be further provided in the follicular cartridge 400c.

Figure 6:
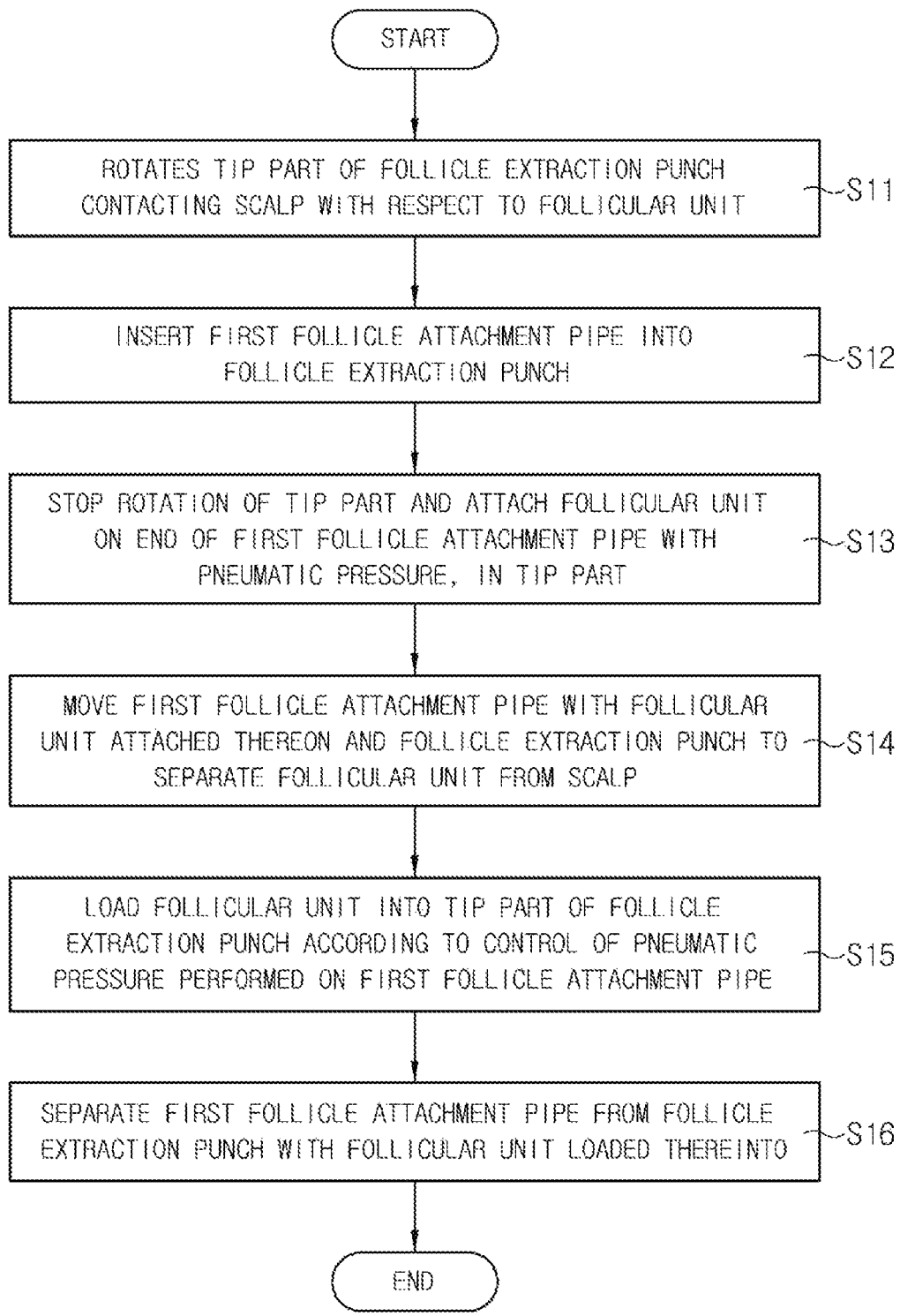
FIG. 6 is a flowchart for describing a method of loading a follicular unit into a needle in a follicle transfer and transplantation method based on FUE according to an application example of the present invention.

FIG. 6 is a flowchart for describing a method of loading a follicular unit into a needle in a follicle transfer and transplantation method based on FUE according to an application example of the present invention. FIGS. 7A to 7F are conceptual diagrams of respective operations of the method illustrated in FIG. 6.

FIG. 6 discloses a method for extracting a follicular unit FU with the follicle extraction punch 100, and immediately, positioning the follicular unit FU in a needle 412 for hair transplantation.

Here, the needle 412 may have an asymmetric tube type structure with respect to a lengthwise direction so as to be used as a needle for hair transplantation and may have a structure where a circular border 412a is provided in one end of the needle 412 and a wedge type border 412b is provided the other end. The wedge type border 412b of the needle 412 enables a slit to be easily formed at a hair transplantation position such as a scalp.

FIGS. 6 to 7F illustrate a method of extracting, by the follicle extraction punch 100, a follicular unit FU and individually locating the follicular unit FU in a needle 412.

Figure 7A:
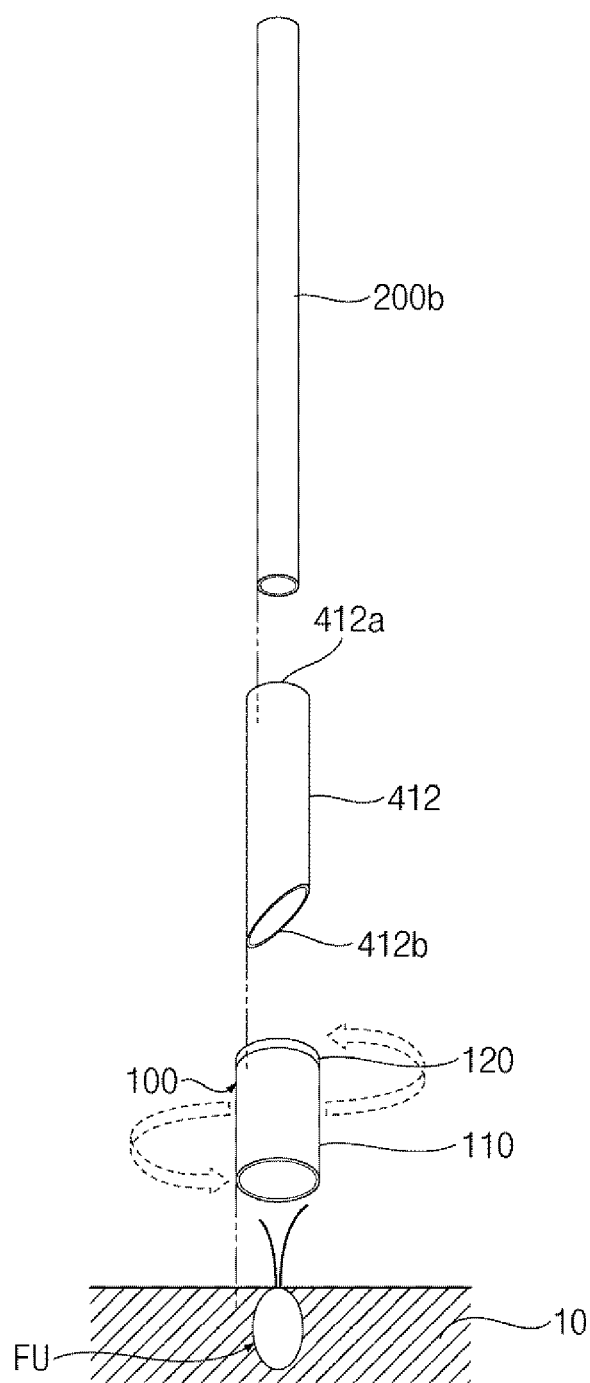

To this end, referring to FIGS. 6 and 7A, an operation (S31) of sequentially setting up the follicle extraction punch 100, the needle 412, and a third follicle attachment pipe 200b with respect to an upper portion of the follicular unit FU may be performed.

Here, an internal diameter of the tip part 110 of the follicle extraction punch 100 may be set relatively greater than an external diameter of the needle 412 in order for interference of the needle 412 not to be applied to a rotation of the tip part 110 performed with respect to a shaft center direction of the needle 412. Also, an internal diameter of the needle 412 may be set relatively greater than an external diameter of the third follicle attachment pipe 200b in order for the third follicle attachment pipe 200b to be inserted into the needle 412.

Figure 7B:
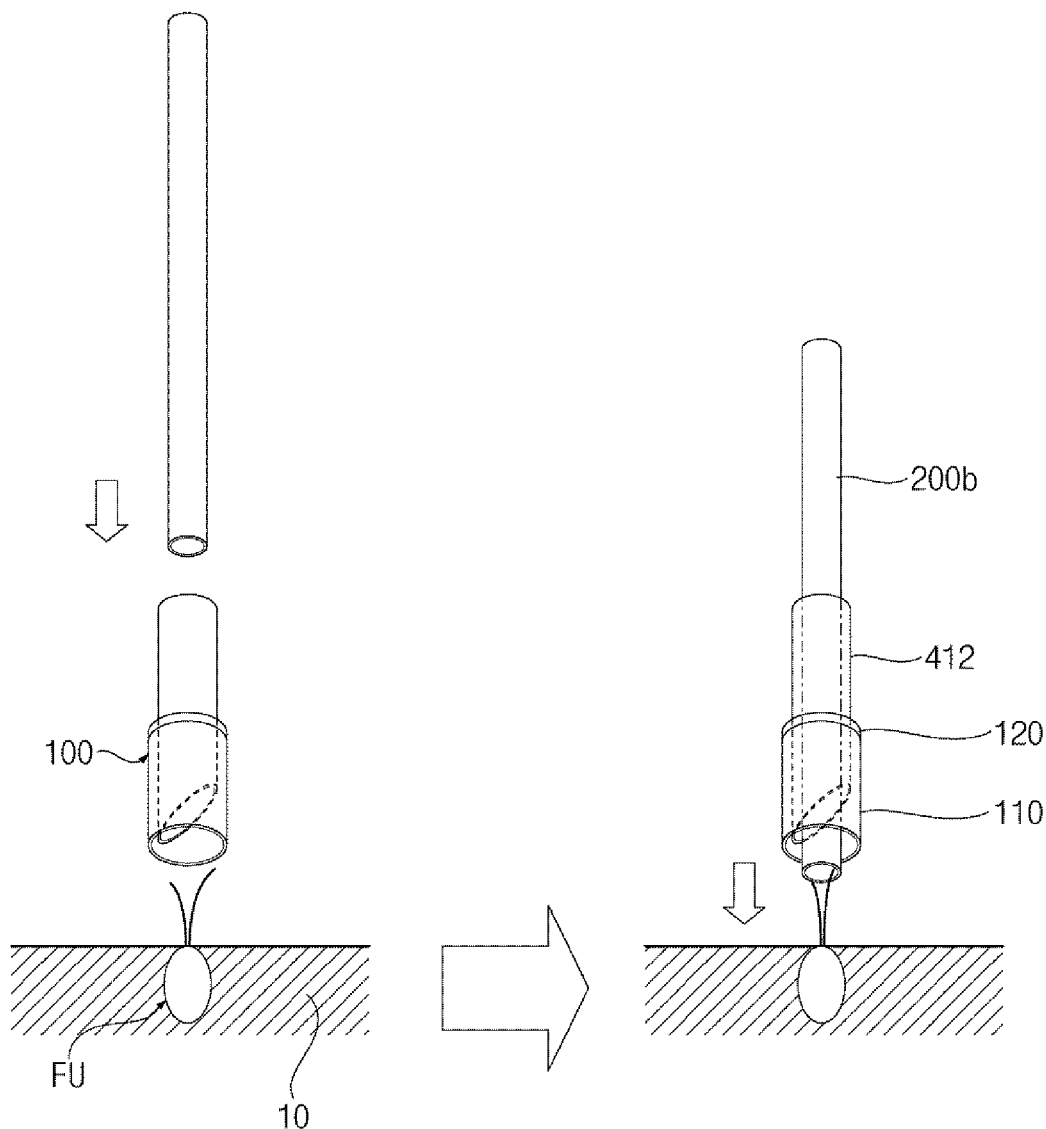

Referring to FIG. 7B, after the setup operation (S31), the third follicle attachment pipe 200b and the needle 412 may be disposed in the follicle extraction punch 100. That is, the needle 412 may be located in the follicle extraction punch 100, and the third follicle attachment pipe 200b may be located in the needle 412 or the third follicle attachment pipe 200b may protrude to a portion under the needle 412.

Figure 7C:
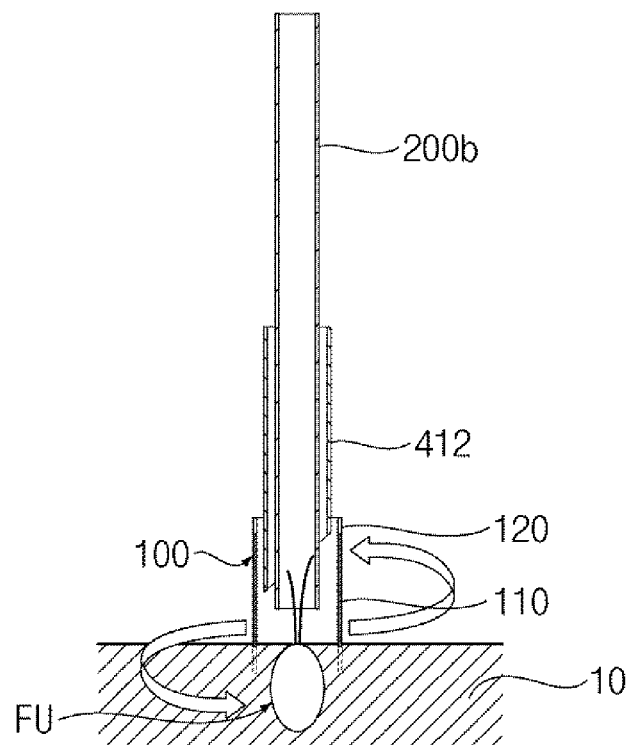

In this state, as in FIG. 7C, the follicle extraction punch 100 may further move downward. Therefore, an operation (S32) of rotating the tip part 110 of the follicle extraction punch 100 contacting the scalp 10 may be performed. In this case, a lower end of the needle 412 and an end of the third follicle attachment pipe 200b in the needle 412 may be separated from the scalp 10 by a predetermined separation distance so as not to contact the scalp 10. Also, the pneumatic pressure P may not be applied to the third follicle attachment pipe 200b, or only a minimum pressure level may be maintained in the third follicle attachment pipe 200b.

Figure 7D:
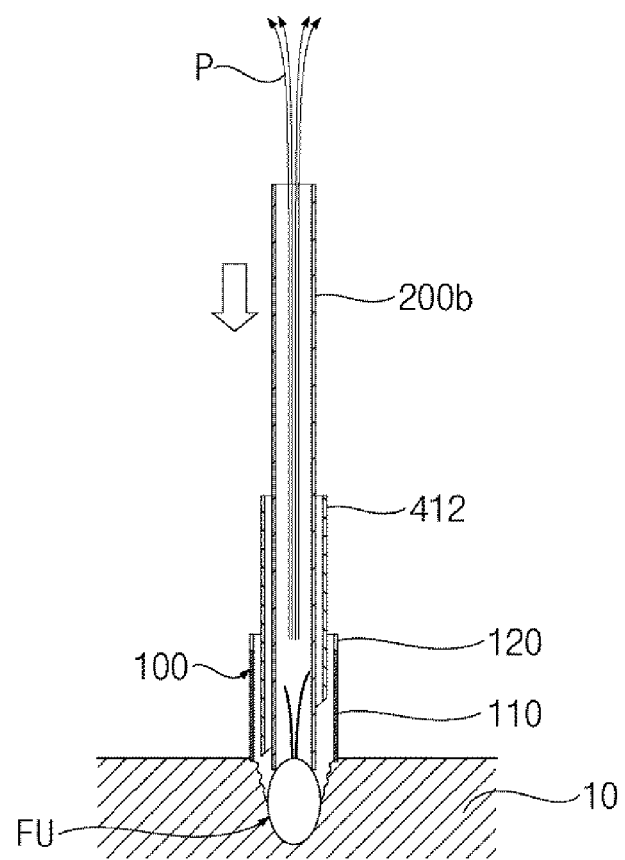

Referring to FIG. 7D, after the rotation operation (S32), an operation (S33) of stopping the rotation of the tip part 110 and further moving the third follicle attachment pipe 200b downward from the inside of the needle 412 to bring an end of the third follicle attachment pipe 200b in contact with the hair bulb member 21 of the follicle unit FU and then attaching the follicular unit FU on the end of the third follicle attachment pipe 200b in the tip part 110 may be performed. The operation (S33) may be performed by the first pneumatic equipment 210, the punch driver 130, and relevant elements described above with reference to FIG. 2A, and thus, a description of a main element performing each operation may be omitted so as not to repeat repetitive descriptions. However, the first pneumatic equipment 210 of FIG. 2A may be modified in order for the pneumatic pressure P to be applied to the inside of the third follicle attachment pipe 200b.

Here, the rotation of the tip part 110 may denote an operation of extracting the follicular unit FU from the scalp 10, namely, a rotational operation or a rotating and raising/lowering complex operation.

Referring to FIG. 7E, after the follicular unit FU is attached on the end of the third follicle attachment pipe 200b, an operation (S34) of moving (for example, raising) the third follicle attachment pipe 200b with the follicular unit FU attached thereon to separate the follicular unit FU from the scalp 10 may be performed.

At this time, the follicle extraction punch 100 may be located in the scalp 10 in a stopped state.

Therefore, a position of the needle 412 is not restrained by the follicle extraction punch 100, or the needle 412 does not excessively move in a lateral direction (for example, a scalp extending direction), thereby providing a condition where the third follicle attachment pipe 200b precisely positions the follicular unit FU in the needle 412.

Subsequently, as in FIGS. 6 and 7F, an operation (S35) of loading the follicular unit FU into the needle 412 through the control of the pneumatic pressure and separating the third follicle attachment pipe 200b and the follicle extraction punch 100 from the needle 412 may be performed.

Accordingly, the needle 412 with the follicular unit FU loaded thereinto may move to a manual hair transplant equipment (not shown) and may be used for hair transplantation, or may be mounted on an automatic hair transplant equipment and may be effectively used for hair transplantation.

FIG. 8 is a conceptual diagram for describing a method of transplanting a follicular unit, loaded by the method of FIG. 1, of a follicle extraction punch to a scalp.

Referring to FIG. 8, a follicle extraction punch 100 with a follicular unit FU loaded thereinto or a follicle extraction punch 100 including the follicular unit FU may be the same as the elements described above with reference to FIGS. 1 to 2F.

The follicle extraction punch 100 including the follicular unit FU may be arranged along with a separate needle 413 for hair transplantation, and then, may be used for a hair transplantation operation for forward moving a push rod 500 to a rod driver 510 of a hair transplant equipment.

The rod driver 510 may be a pusher that raises or lowers the push rod 500 or backward or forward moves the push rod 500, or may be a device for realizing a pushing operation.

That is, when the push rod 500 forward moves (for example, downward moves) according to an operation of the rod driver 510, the follicular unit FU may be loaded from the inside of the follicle extraction punch 100 to the separate needle 413 for hair transplantation, or may be transplanted into a scalp 11 via the needle 413.

For example, referring to FIG. 1, after the operation (S15) of loading the follicular unit into the tip part of the follicle extraction punch, as illustrated in FIG. 8, the follicle extraction punch 100 including the follicular unit FU may be disposed between the needle 413 for hair transplantation and the push rod 500 moving the follicular unit FU in the hair transplant equipment, and the push rod 500 may forward move toward the inside of the follicle extraction punch 100, whereby the follicular unit FU of the follicle extraction punch 100 may be pushed by the push rod 500 to move and may be transplanted into the scalp 11 via the inside of the needle 413 for hair transplantation. Such an operation may be performed.

FIG. 9 is a conceptual diagram for describing a method of transplanting a follicular unit, loaded by the method of FIG. 3, from a follicle extraction punch to a scalp.

FIG. 9 exemplarily illustrates a follicular unit transplantation method performed after follicular units FU are all loaded into a plurality of needles 410 and 411 of a follicular cartridge 400 by repeatedly performing the operations described above with reference to FIGS. 3 and 4A to 4F.

For example, an operation of FIG. 9 may be performed after the operation (S25) of changing a position of a follicular cartridge in FIG. 3.

At this time, the follicular cartridge 400 including a plurality of needles 410 into which follicular units FU are respectively loaded may be separated from the cartridge driver 420 of FIG. 4E and may be mounted on a hair transplant equipment (for example, an automatic hair transplant equipment), whereby the follicular cartridge 400 may be disposed between the needle 413 for hair transplantation and the push rod 500 moving the follicular unit FU in the hair transplant equipment. Also, the push rod 500 may forward move toward the inside of the needle 410 of the follicular cartridge 400, and thus, the follicular unit FU of the needle 410 of the follicular cartridge 400 may be pushed by the push rod 500 to move and may be transplanted into the scalp 11 via the inside of the needle 413 for hair transplantation. Such an operation may be performed.

Here, the automatic hair transplant equipment may be a hair transplant equipment having an automatic follicle supply function disclosed in the patent document 2, and in this case, the details described above in the present embodiment can more increase the utility of various continuous automatic supply disclosed in the patent document 2.

The follicle transfer and transplantation method based on FUE according to the embodiments of the present invention may provide detailed follicle transfer methods for loading a follicular unit to a follicle extraction punch or a needle immediately after the follicular unit vegetating in a scalp is extracted, thereby considerably simplifying a process of extracting, transferring, and transplanting the follicular unit and shortening a time taken in the extracting, transferring, and transplanting process.

Moreover, in the follicle transfer and transplantation method based on FUE according to the embodiments of the present invention, since a follicular unit is quickly loaded to a follicle supply unit or a follicle supply pipe of the related art, the manufacturing efficiency of a follicular cartridge necessary for a hair transplant equipment for hair transplantation increases, and the use of the hair transplant equipment for hair transplantation is largely activated.

Moreover, in the follicle transfer and transplantation method based on FUE according to the embodiments of the present invention, since a follicular unit is loaded into a follicle extraction punch or a needle immediately after the follicular unit is extracted, an operation time taken in transferring an extracted follicle into a vessel or the like is reduced in comparison with the related art, or the damage of a follicle which occurs in a process of transferring or collecting a follicular unit to or in a follicle supply means such as the follicle supply unit or the follicle supply pipe described in the background after the follicular unit is collected in a vessel is minimized in comparison with the related art.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A follicle transfer and transplantation method based on follicular unit extraction (FUE) for extracting a follicular unit to individually locate the follicular unit in a needle, the follicle transfer and transplantation method comprising:
    rotating a tip part of a follicle extraction punch contacting a scalp with respect to the follicular unit;
    inserting a follicle attachment pipe into the follicle extraction punch;
    stopping the rotation of the tip part and attaching the follicular unit on an end of the follicle attachment pipe with a pneumatic pressure, in the tip part;
    moving the follicle attachment pipe with the follicular unit attached thereon and the follicle extraction punch to separate the follicular unit from the scalp;
    loading the follicular unit into the tip part of the follicle extraction punch according to control of the pneumatic pressure performed on the follicle attachment pipe; and
    separating the follicle attachment pipe from the follicle extraction punch with the follicular unit loaded thereinto.

2. The follicle transfer and transplantation method of claim 1, wherein the follicle extraction punch comprises:
    the tip part supplied with a rotational force from a punch driver for extracting the follicular unit from the scalp; and
    a pipe member connecting connector provided in an end of the tip part.

3. The follicle transfer and transplantation method of claim 2, further comprising: before the rotating of the tip part, movably locating the follicle attachment pipe on the follicle extraction punch in a state where a shaft center direction of the follicle attachment pipe matches a shaft center direction of the follicle extraction punch.

4. The follicle transfer and transplantation method of claim 3, wherein an internal diameter of the tip part of the follicle extraction punch is set relatively greater than an external diameter of the follicle attachment pipe so that interference of the follicle attachment pipe is not applied to the rotation of the tip part performed with respect to the shaft center direction of the follicle attachment pipe.

5. The follicle transfer and transplantation method of claim 4, wherein the follicle attachment pipe is coupled to a pneumatic equipment which generates the pneumatic pressure in the follicle attachment pipe.

6. The follicle transfer and transplantation method of claim 1, further comprising: after the loading of the follicular unit, locating the follicle extraction punch including the follicular unit between a needle for hair transplantation and a push rod moving the follicular unit in a hair transplant equipment, forward moving the push rod toward the inside of the follicle extraction punch, moving the follicular unit of the follicle extraction punch according to the follicular unit being pushed by the push rod, and transplanting the follicular unit into the scalp via the inside of the needle for hair transplantation.

7. A follicle transfer and transplantation method based on follicular unit extraction (FUE) for extracting a follicular unit to individually locate the follicular unit in a needle, the follicle transfer and transplantation method comprising:
connecting a transfer pipe and a follicle attachment pipe and passing through the inside of an empty needle of a follicle cartridge and connecting a follicle extraction punch, into which the follicular unit has been loaded, to the transfer pipe;
transferring the follicular unit from the inside of the follicle extraction punch to the inside of the transfer pipe;
attaching the follicular unit on an end of the follicle attachment pipe, in the transfer pipe;
moving an end of the follicle attachment pipe with the follicular unit attached thereon from the inside of the transfer pipe to the inside of an empty needle and loading the follicular unit into the empty needle by controlling a pneumatic pressure;
separating the follicle attachment pipe from the needle for which loading ends, and changing a position of the follicular cartridge so that a shaft center of the follicle attachment pipe matches a shaft center of an empty needle corresponding to a next order; and
inserting the follicle attachment pipe into the empty needle corresponding to the next order by moving the follicle attachment pipe toward the follicular cartridge disposed at the changed position.

8. The follicle transfer and transplantation method of claim 7, wherein the follicle attachment pipe is coupled to a pneumatic equipment which generates the pneumatic pressure in the follicle attachment pipe.

9. The follicle transfer and transplantation method of claim 8, wherein the follicle extraction punch comprises:
a tip part separated from a punch driver which is a rotational force generation means for extracting the follicular unit from the scalp, the tip part including an internal space into which the follicular unit is loaded; and
a pipe member connecting connector provided in an end of the tip part, for connecting the follicle extraction punch to the transfer pipe.

10. The follicle transfer and transplantation method of claim 9, wherein the transfer pipe comprises:
a connector coupling part provided in one end of the transfer pipe, for attaching or detaching the pipe member connecting connector of the follicle extraction punch;

a pipe body part extending in a direction from the connector coupling part to the follicular cartridge and acting as a transfer path for the follicular unit; and
a transfer pipe coupling part provided in another end of the transfer pipe and connected to the pipe body part to pass through the pipe body part, so that the transfer pipe coupling part becomes an entrance which an end of the follicle attachment pipe is inserted through or detached from.

11. The follicle transfer and transplantation method of claim 7, wherein the follicular cartridge is detachably attached on a cartridge driver which changes a position of the follicular cartridge along a direction vertical to a moving direction of the follicle attachment pipe, with respect to a position between the transfer pipe and the follicle attachment pipe.

12. The follicle transfer and transplantation method of claim 11, further comprising: after the changing of the position of the follicular cartridge, separating the follicular cartridge, including a plurality of needles into which follicular units are respectively loaded, from the cartridge driver, mounting the separated follicular cartridge on a hair transplant equipment, locating the follicular cartridge between a needle for hair transplantation and a push rod moving the follicular unit in the hair transplant equipment, forward moving the push rod toward the inside of the needle of the follicular cartridge, moving the follicular unit of the needle of the follicular cartridge according to the follicular unit being pushed by the push rod, and transplanting the follicular unit into the scalp via the inside of the needle for hair transplantation.

13. A follicle transfer and transplantation method based on follicular unit extraction (FUE) for extracting a follicular unit to individually locate the follicular unit in a needle, the follicle transfer and transplantation method comprising:
sequentially setting up a follicle extraction punch, a needle, and a follicle attachment pipe with respect to an upper portion of the follicular unit;
rotating a tip part of the follicle extraction punch contacting a scalp in a state where the follicle attachment pipe and the needle are disposed in the follicle extraction punch;
stopping the rotation of the tip part and attaching the follicular unit on an end of the follicle attachment pipe with a pneumatic pressure, in the tip part;
moving the follicle attachment pipe with the follicular unit attached thereon to separate the follicular unit from the scalp; and
loading the follicular unit into the needle through control of the pneumatic pressure and separating the follicle attachment pipe and the follicle extraction punch from the needle.

14. The follicle transfer and transplantation method of claim 13, wherein
an internal diameter of the tip part of the follicle extraction punch is set relatively greater than an external diameter of the needle so that interference of the needle is not applied to the rotation of the tip part performed with respect to a shaft center direction of the needle, and
an internal diameter of the needle is set relatively greater than an external diameter of the follicle attachment pipe so that the follicle attachment pipe is inserted into the needle.

15. The follicle transfer and transplantation method of claim 14, wherein the needle has a structure where a circular border is provided in one end of the needle and a wedge type border is provided another end, so as to be used as a needle for hair transplantation.

16. The follicle transfer and transplantation method of claim 14, wherein the needle has a structure where a circular border is provided in each of one end and another end of the needle, so as to be used as a needle for hair transplantation.

\* \* \* \* \*